(12) United States Patent
Matsumoto et al.

(10) Patent No.: US 9,679,738 B2
(45) Date of Patent: Jun. 13, 2017

(54) ELECTRON MICROSCOPE

(71) Applicant: Hitachi High-Technologies Corporation, Minato-ku, Tokyo (JP)

(72) Inventors: Hiroaki Matsumoto, Tokyo (JP); Takeshi Sato, Tokyo (JP); Yoshifumi Taniguchi, Tokyo (JP); Ken Harada, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/916,529

(22) PCT Filed: May 16, 2014

(86) PCT No.: PCT/JP2014/063016
§ 371 (c)(1),
(2) Date: Mar. 3, 2016

(87) PCT Pub. No.: WO2015/045476
PCT Pub. Date: Apr. 2, 2015

(65) Prior Publication Data
US 2016/0196952 A1     Jul. 7, 2016

(30) Foreign Application Priority Data

Sep. 30, 2013   (JP) ................................ 2013-202951

(51) Int. Cl.
*H01J 47/00*      (2006.01)
*H01J 37/10*      (2006.01)
(Continued)

(52) U.S. Cl.
CPC ........ *H01J 37/10* (2013.01); *G01N 23/20058* (2013.01); *H01J 37/04* (2013.01);
(Continued)

(58) Field of Classification Search
None
See application file for complete search history.

(56) References Cited

U.S. PATENT DOCUMENTS

| | | | |
|---|---|---|---|
| 4,851,677 A * | 7/1989 | Hosoi | H01J 37/224 250/397 |
| 2004/0061053 A1* | 4/2004 | Taniguchi | G01L 1/241 250/310 |

(Continued)

FOREIGN PATENT DOCUMENTS

| JP | 4-137344 A | 5/1992 |
|---|---|---|
| JP | 4137344 B2 * | 8/2008 |

(Continued)

OTHER PUBLICATIONS

International Search Report (PCT/ISA/210) issued in PCT Application No. PCT/JP2014/063016 dated Jul. 15, 2014 with English translation (four pages).

(Continued)

*Primary Examiner* — Andrew Smyth
(74) *Attorney, Agent, or Firm* — Crowell & Moring LLP

(57) ABSTRACT

The present invention relates to a lens-less Foucault method wherein a transmission electron microscope objective lens (5) is turned off, an electron beam crossover (11, 13) is matched with a selected area aperture (65), and the focal distance of a first imaging lens (61) can be changed to enable switching between a sample image observation mode and a sample diffraction pattern observation mode, characterized in that a deflector (81) is disposed in a stage following the first imaging lens (61), and conditions for an irradiating optical system (4) can be fixed after conditions for the imaging optical system have been determined. This allows a lens-less Foucault method to be implemented in a common general-use transmission electron microscope with no magnetic shielding lens equipped, without burdening the operator.

16 Claims, 22 Drawing Sheets

(51) Int. Cl.
| | |
|---|---|
| H01J 37/295 | (2006.01) |
| H01J 37/04 | (2006.01) |
| H01J 37/26 | (2006.01) |
| G01N 23/20 | (2006.01) |
| H01J 37/09 | (2006.01) |
| H01J 37/147 | (2006.01) |
| H01J 37/153 | (2006.01) |
| H01J 37/24 | (2006.01) |
| H01J 37/244 | (2006.01) |
| H01J 37/28 | (2006.01) |
| H01J 37/05 | (2006.01) |
| H01J 37/285 | (2006.01) |

(52) U.S. Cl.
CPC .............. *H01J 37/05* (2013.01); *H01J 37/09* (2013.01); *H01J 37/147* (2013.01); *H01J 37/1472* (2013.01); *H01J 37/153* (2013.01); *H01J 37/24* (2013.01); *H01J 37/244* (2013.01); *H01J 37/26* (2013.01); *H01J 37/261* (2013.01); *H01J 37/28* (2013.01); *H01J 37/285* (2013.01); *H01J 37/295* (2013.01); *G01N 2223/418* (2013.01); *H01J 2237/21* (2013.01); *H01J 2237/2614* (2013.01)

(56) References Cited

U.S. PATENT DOCUMENTS

| | | | |
|---|---|---|---|
| 2010/0252735 A1* | 10/2010 | Hytch | H01J 37/26 250/311 |
| 2011/0031395 A1* | 2/2011 | Harada | H01J 37/28 250/307 |
| 2014/0197312 A1* | 7/2014 | Harada | H01J 37/26 250/307 |

FOREIGN PATENT DOCUMENTS

| | | | |
|---|---|---|---|
| JP | 2010-540895 A | | 12/2010 |
| JP | 2011-40217 A | | 2/2011 |
| JP | 2011040217 A | * | 2/2011 |
| JP | 2012-199022 A | | 10/2012 |
| JP | 2012199022 A | * | 10/2012 |
| WO | WO 2013/046277 A1 | | 4/2013 |

OTHER PUBLICATIONS

Chapman, "The investigation of magnetic domain structures in thin foils by electron microscopy" J. Phys. D: Appl. Phys, 1984, pp. 623-647, Department of Natural Philosophy, University of Glasgow, Glasgow, UK.

Harada, "Twin-Foucault imaging method" Applied Physics Letter 100, 2012, four pages, American Institute of Physics.

Taniguchi et al., "Foucault imaging by using non-dedicated transmission electron microscope" Applied Physics Letters 101, 2012, five pages, American Institute of Physics.

Tonomura, "Applications of Electron Holography Using a Field-Emission Electron Microscope" J. Electron Microsc., 1984, pp. 101-115, vol. 33, No. 2, Central Research Laboratory et al., Kokubunji, Tokyo, Japan.

Ishizuka et al., "Phase measurement of atomic resolution image using transport of intensity equation" Journal of Electron Microscopy 54(3), 2005, pp. 191-197, Oxford University Press.

Koyama et al., "Small angle electron diffraction and deflection" AIP Advances 2, 2012, eight pages, American Institute of Physics.

Wade, "Electron Diffraction from a Magnetic Phase Grating" 1967, pp. 847-854.

Japanese-language Written Opinion (PCT/ISA/237) issued in PCT Application No. PCT/JP2014/063016 dated Jul. 15, 2014 (four pages).

* cited by examiner

ELECTRON MICROSCOPE

TECHNICAL FIELD

The present invention relates to an electron microscope, and a sample observation method using the electron microscope.

BACKGROUND ART

A Lorenz microscope method has been developed as a method of observing a behavior of deflecting an electron beam transmitting a magnetic material by receiving a Lorenz force by magnetizing a sample as its name signifies. However, currently, the method is received as a method of visualizing a deflection state of an electron beam, or a method of visualizing an electron beam receiving a deflection by an interactive operation different from Bragg diffraction caused by a crystal structure not only for the magnetic material but a dielectric polarization, a strain field or the like. Roughly classified, there are two methods of a Foucault method and a Fresnel method in the Lorenz method (Nonpatent Literature 1), in term of the magnetic material, the Fresnel method is a method of observing a domain wall, and the Foucault method is a method of observing a magnetic domain.

In the following, an explanation will be given of respective methods of the Fresnel method and the Foucault method by taking an example of observing the magnetic material having a 180-degree inversion magnetic domain structure. Further, a simple description will be given to electron beam holography, an intensity transportation equation method, and a small angle diffraction method as examples of other method of methods of visualizing a small deflection electron beam using a transmission electron microscope.

<Fresnel Method>

FIG. 1 shows a behavior of an electron beam receiving a deflection by a magnetic material having a 180-degree inversion magnetic domain structure. An angle of deflecting an electron beam depends on a magnitude of a magnetization and a thickness of a sample. Therefore, in a case of a sample having a constant thickness and a uniform magnetization, the angle of deflection received by the electron beam stays the same in any domain, and an azimuth and a direction differ in accordance with a magnetic domain structure. As shown in FIG. 1, when electron beams 27 are incident on a sample 3 having the 180-degree inversion magnetic domain structure, the electron beams 27 transmitting the sample 3 receive deflections in inverse directions by the respective magnetic domains (31, 33). When the electron beams 27 receiving the deflections are propagated by sufficient distances below the sample, there are generated a situation of overlapping each other and a situation of separating from each other inversely on a projected face 24 at positions in correspondence with 180° magnetic walls 32. The Fresnel method focuses condensation and rarefaction of an intensity of the electron beam on the projected face 24. A graph 25 of an intensity distribution of an electron beam on the projected face is exemplified at a lower portion of FIG. 1.

FIG. 2 is a schematic view of an optical system when a magnetic material is observed by the Fresnel method. A Fresnel image 86 is exemplified at a lower portion of FIG. 2. FIG. 2A shows a behavior of observing by focusing not a sample but a space position 35 on a lower side of the sample, and a portion of exactly the magnetic wall 32 is observed by a contrast 72 of a bright line (white color) or a dark line (black color). Similarly, as shown in FIG. 2B, even when a space position 36 on an upper side of the sample is focused, a portion of the magnetic wall 32 is observed by an inverse contrast 72. That is, a boundary line of a domain giving a deflection to an electron beam is observed by a bright line (white color) or a dark line (black color) by observing the sample by defocusing the sample. A white and black contrast of the boundary line of the Fresnel image at this occasion depends on a combination of the deflection direction and a position of focusing. Also, an amount of defocusing (defocusing amount) depends on a magnitude of a deflection received by an electron beam, and although in a case of a large deflection, a sufficient contrast is obtained by a small defocusing amount of about several hundreds nm, in a case of an observation object giving only a small deflection as in, for example, a fluxoid quantum, a defocusing amount of several hundreds nm is needed.

<Foucault Method>

FIG. 3 shows an optical system of observing a magnetic domain structure by a Foucault method. Similarly to FIG. 1, electron beams transmitting the sample 3 having the 180-degree inversion magnetic domain structure receive deflections in directions inverse to each other by the respective magnetic domains (31, 33), and the electron beams receiving the deflections in the directions are spotted (11, 13) at positions in accordance with deflection angles thereof at, for example, a rear focal point face 54 of an objective lens 5 (strictly speaking, an image face of a light source by the objective lens). Hence, an objective aperture 55 is inserted and only an electron beam transmitting a magnetic field intended to observe is selected and focused on an image face 7. For example, in FIG. 3A, this is an example of selecting an electron beam transmitting through the magnetic domain 31 and deflected in an upper left direction of paper face, and FIG. 3B shows an example of selecting an electron beam inversely transmitting through the magnetic domain 33 and deflected in an upper right direction on paper face. At any rate, a magnetic domain which is selected is observed in white color, and a magnetic domain which is not selected is observed in black color (electron beam does not come), and in a case of a 180-degree inversion magnetic domain structure, the respective magnetic domains (31, 33) are visualized as Foucault images 84 in stripe shapes (71, 73).

Although in the Foucault method, the sample image is observed in focus, and therefore, a high resolution observation is expected, for example, in a case of a magnetic material, the deflection angle of the electron beam is as small as about 1/10 of a Bragg angle by the crystalline sample, and therefore, an objective aperture having a small aperture diameter needs to be used, and an obtained spatial resolution is about 1/10 times as much as a lattice resolution, which is not significantly different from that in the Fresnel method. Further, an origin of a contrast for observing the magnetic domain structure is caused by shielding an electron beam which is transmitted through a magnetic field which is not observed, and this has been a method of obtaining the contrast by abandoning a portion of information. Therefore, for example, in a case of observing an object extending plural magnetic domains as in crystal drain boundaries, it is necessary to readjust the objective aperture and separately observe the Foucault image having an inverse contrast, or an ordinary electron microscope image needs to be observed additionally by deviating the objective aperture from an optical axis. That is, observations at plural times are needed, and a dynamic observation, a real time observation or the like has substantially been impossible.

As one of methods of dealing with a defect by the Foucault method described above, although an illustration is omitted, there is proposed a method of further deflecting the propagation angle of the electron beam receiving the deflection by the sample by using an electron beam biprism in an irradiating optical system, and observing and recording plural Foucault images once by focusing the images at locations different from each other on the observation face (twin Foucault method) (Patent Literature 1) (Nonpatent Literature 2). The method proposes a new concept of one mirror two images (information), in implementing the Foucault method, conditions to be added to a conventional Lorenz electron microscope of not only the magnetic shielding lens but the electron beam biprism or the like are increased in implementing the Foucault method. Therefore, it seems that a small period of time is taken for spreading the method.

<Lens-Less Foucault Method>

In recent times, there has been developed a method of enabling to implement the Foucault method and the small angle electron diffraction by using an ordinary general-use transmission electron microscope which does not include a magnetic shielding lens (Nonpatent Literature 3). This is the lens-less Foucault method. The "lens-less" described here signifies that an objective lens is turned off and is not used for focusing. A description will be given later of details of the method. (Incidentally, the present invention has been carried out for executing an effective experiment by alleviating a burden of an electron microscope operator in operating the device in implementing the lens-less Foucault method, and relates to a control of an optical system by the lens-less Foucault method.)

<Other Lorenz Method>

Other than the Lorenz microscope method described above, there have been developed electron beam holography (Nonpatent Literature 4), an intensity transportation equation method (Nonpatent Literature 5) and the like as methods of observing the magnetic domain structure of the sample from a phase distribution of an electron beam. Although any of the methods have respective advantages, it is an actual situation that there are a number of complications in implementing the methods such that an electron beam having a high coherence of an electric field emission type electron beam is needed, an electron beam biprism is needed as an additional device in the electron beam holography, a domain for transmitting a reference wave needs to be considered in a sample shape, at least 2 sheets of images defocusing amounts of which are already known are needed by interposing an image in focus (a total of three sheets of images) in the intensity transportation equation method, and magnifications and an adjusting process of positioning or the like for respective images are indispensable and so on.

<Small Angle Diffraction Method>

In recent times, the method of observing a deflection angle of the electron beam by a magnetization in a sample as a diffraction spot at a diffraction face has begun to be implemented (Nonpatent Literature 6). The method is a method of observing the small diffraction angle of the electron beam as a diffraction pattern at a diffraction face (that is, as a diffraction pattern of a large camera length), which was implemented in 1960 year generation (Nonpatent Literature 7), and this is a technology which has been forgotten for a long time thereafter. This is a method which is effective for obtaining information of an average deflection angle, which is reconsidered as a method of detecting a deflection angle of a transmission electron beam receiving from an entire irradiating area of the electron beam which is an average value rather than detecting a small deflection angle of a transmission electron by an individual element when the deflection angle of the electron beam is reduced by miniaturizing and thinning a magnetic element.

Table 1 summarizes a main observation object, a deflection angle received by an electron beam of an acceleration voltage 300 kV, and a camera length needed for observation.

TABLE 1

Deflection angle received by 300 kV electron beam and camera length needed for observation

| Observation object | Deflection angle of electron beam (rad) | Camera length needed for observation (m) |
|---|---|---|
| Crystal (Bragg diffraction) | $10^{-2}$ | $10^{0}$ |
| Long period structure | $10^{-3}$ | $10^{1}$ |
| Magnetic body (magnetic domain) | $10^{-4}$ through $10^{-5}$ | $10^{2}$ through $10^{3}$ |
| Dielectric substance (dielectric polarization) | $10^{-5}$ through $10^{-6}$ | $10^{3}$ through $10^{4}$ |
| Metal superconductor fluxoid quantum | $10^{-6}$ through $10^{-7}$ | $10^{4}$ through $10^{5}$ |
| High temperature superconductor fluxoid quantum | $10^{-7}$ or less | $10^{5}$ or more |

<Foucault Method and Small Angle Diffraction Method>

As described above, it is necessary for optimally implementing the Foucault method to pertinently use an angle restricting aperture at a diffraction face. For example, in a case of a magnetic material (magnetization 1 T (tesla)) having a thickness of 50 nm which can be easily transmitted by an electron beam of an acceleration voltage 300 kV, a deflection angle by a magnetism becomes about $2\times10^{-5}$ rad, which is an angle nearly 1,000 times smaller than a Bragg diffraction angle by crystal. Therefore, in the Foucault method, it is necessary to be able to realize the small angle diffraction method as a matter of fact for improving a focusing accuracy thereof. That is, it is necessary to construct an optical system such that a diffraction pattern having a large camera length in correspondence with the small angle diffraction is formed (it is necessary to construct an optical system which can magnify the diffraction pattern). Moreover, it is necessary that a diffraction face of a diffraction pattern and a face of inserting an angle restriction aperture coincide with each other.

Although an explanation has been given of the Lorenz method as a magnetic material observing method by a transmission electron microscope as described above, the observation object is not limited to the magnetic material as described above. Above all, in a view point of visualizing or focusing an electron beam having a small deflection angle, the method has a technical side view which is common also to a phase difference electron microscope method for a biological sample, an organic sample or the like.

CITATION LIST

Patent Literature

Patent Literature 1: W02013/046277A

Nonpatent Literature

Nonpatent Literature 1: J. N. Chapman, J. Phys. D., Appl. Phys., 17, 623 (1984).

Nonpatent Literature 2: K. Harada, Appl. Phys. Lett., 100, 061901 (2012).
Nonpatent Literature 3: Y. Taniguchi, A. Matsumoto and K. Harada, Appl. Phys Lett., 101, 093101 (2012).
Nonpatent Literature 4: A. Tonomura, J. Electron Microsc., 33, 101 (1984)
Nonpatent Literature 5: K. Ishizuka and B. Allman, J. Electron Microsc. 54, 191 (2005).
Nonpatent Literature 6: T. Koyama, et al., AIP Advances, 2, 012195 (2012).
Nonpatent Literature 7: R. H. Wade, Phys. Stat. Sol., 19, 847 (1967).

SUMMARY OF INVENTION

Technical Problem

In a lens-less Foucault method realizing the Lorenz method, particularly the Foucault method in an ordinary general use type transmission electron microscope which does not mount the magnetism shielding lens, there are a number of restrictions in comparison with a conventional observation method such that an angle restriction aperture needs to be applied to a sample transmission electron beam in a state of turning off an objective lens, and concerning a condition of using an electron optical system, for example, an irradiating optical system is not changed after confirming an observation condition, switching of an image observation mode of a sample and a diffraction pattern observation mode of the sample is realized with excellent reproducibility, and in the switching, the irradiating optical system is not changed, and so on, and a burden of the electron microscope operator in operating tends to be increased.

In the Foucault method, in order to obtain information concerning a diffraction spot which does not contribute to focusing, plural times of experiments need to be repeated such that as a procedure, an optical system is brought into a diffraction pattern observation mode, thereafter, a diffraction pattern is confirmed and an angle restriction aperture is properly inserted, the optical system is switched to the image observation mode and the Foucault sample image is observed and recorded, the optical system is brought again into the diffraction pattern observation mode, the diffraction spot which is different from that of previous observation is properly adopted to the angle restriction aperture, the optical system is brought again into the image observation mode and the Foucault image is observed and recorded, further, the optical system is brought into the diffraction pattern observation mode and so on. In such an experimental situation, the alleviation of the burden in operating the electron microscope is an important factor in executing a high quality experiment.

Solution to Problem

The present invention relates to a control method, a control condition and the like which are executed for alleviating a burden of the electron microscope operator in operating. For example, although in the lens-less Foucault method, the irradiating optical system needs to be changed after confirming the observation condition, a control method is executed such that by introducing an operation for fixing a condition of an irradiating lens, an erroneous operation after confirming a condition of using the irradiating optical system is prevented, in switching the observation mode of the optical system, by memorizing an exciting condition of the imaging lens, a lens condition immediately after switching is made to coincide with a final observation condition of the mode at a previous time and so on. Thereby, an electron microscope or an observation method in which the lens-less Foucault method can be executed without burdening the electron microscope operator is provided.

Advantageous Effects of Invention

By the present invention, in executing the lens-less Foucault method in which only the objective lens is turned off by using a general use type transmission electron microscope and any additional device is not needed, for example, occurrences of time and labor of readjusting the optical system by an erroneous operation are reduced, and a burden of the electron microscope operator in operating can be reduced to a degree the same as a conventional electron microscope operation. That is, the lens-less Foucault method can simply be executed. Further, the simplicity of the execution produces effects of shortening time required for readjusting the optical system in executing the experiment, improvement in an accuracy of the optical system adjustment, improvement of the reproducibility, an observation experiment of plural images in which the diffraction spot generated in principle in the Foucault method is changed is facilitated, an accuracy of an experimental data (Foucault image) is improved, and a reliability of the experiment per se is improved.

DESCRIPTION OF EMBODIMENTS

The present invention has been carried out concerning an operating method effective for operating an electron microscope, an adjusting method of an optical system, and an experimental method thereby in constructing and switching an optical system observing an image of an sample and an optical system observing a diffraction pattern of the sample in a lens-less Foucault method which can execute a Foucault method without using an objective lens in a general use type electron microscope. At first, an explanation will be given of a less-less Foucault method (Nonpatent Literature 3).
<Lens-Less Foucault Method>

Figure 4:
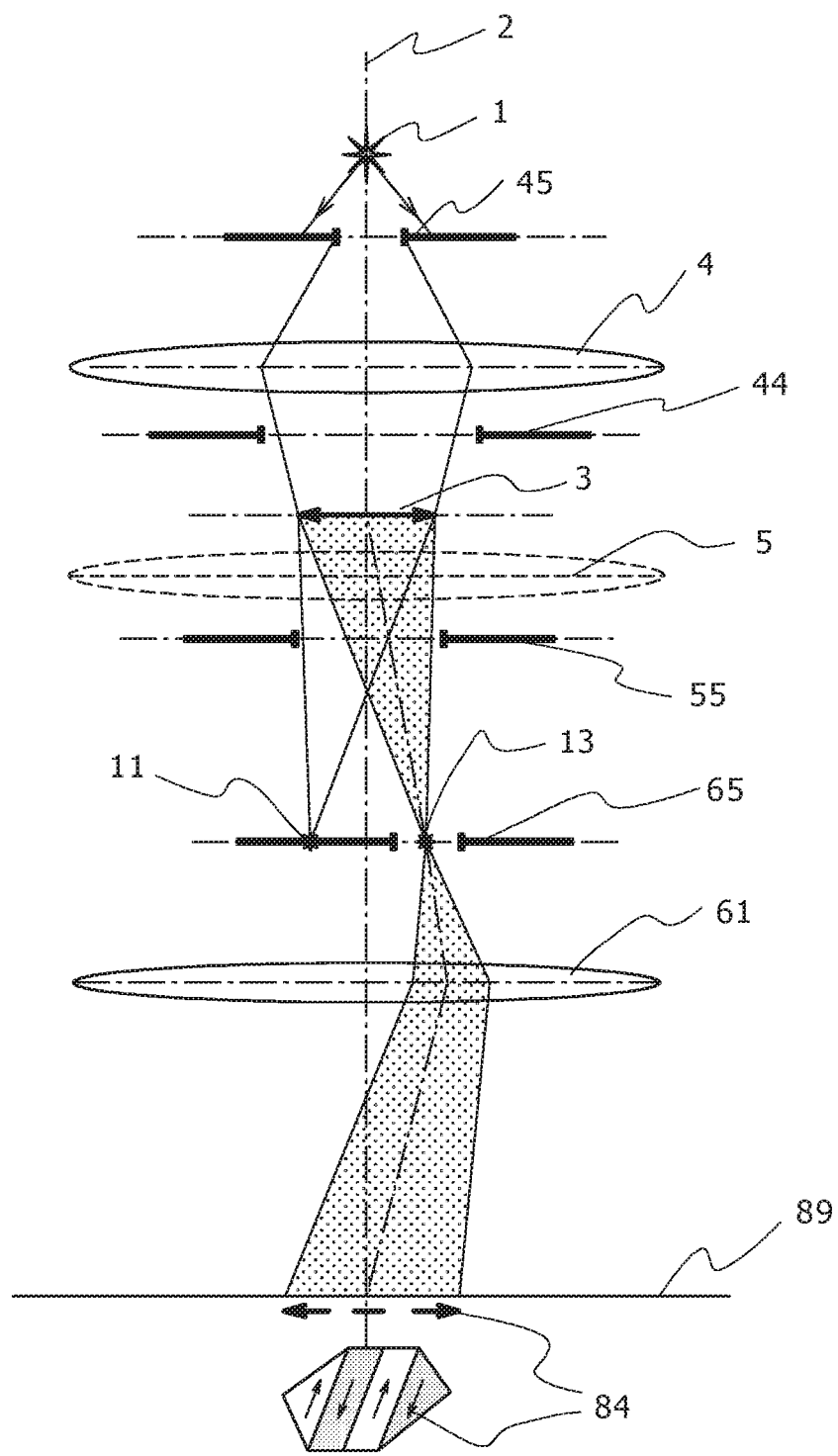
FIG. 4 is a schematic view for explaining Foucault image observation in a lens-less Foucault method.
Figure 5:
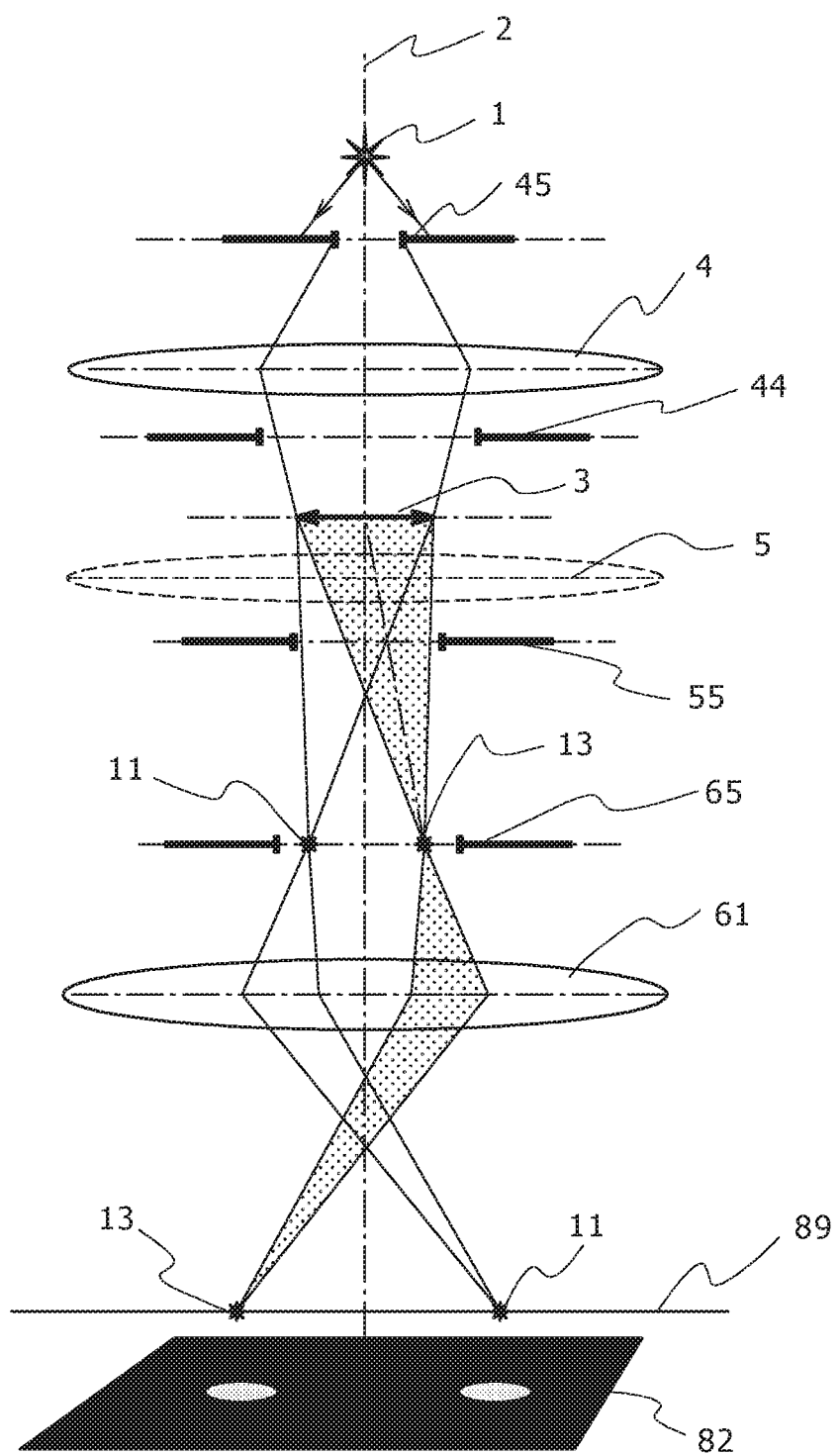
FIG. 5 is a schematic view for explaining a small angle diffraction pattern observation in a lens-less Foucault method.

A lens-less Foucault method has been developed as an optical system which can realize a Foucault method by using a general use type electron microscope without using a magnetic shielding objective lens by a Lorenz electron microscope. In an ordinary Foucault method, a crossover of an electron beam transmitted through a sample by a magnetic shielding objective lens is focused on an objective aperture face, and a deflection angle separation of the electron beam is controlled by a size and an insertion position of an objective aperture. On the other hand, in the lens-less Foucault method, the objective lens is turned off (therefore, a sample is not immersed in a magnetic field), and the crossover of the electron beam transmitting the sample is focused on a selected area aperture face in an ordinary case (an image face of the sample by the objective lens in an ordinary case) by an irradiating optical system in place of the objective lens. Further, a deflection angle separation of the electron beam is executed by using the restricting visual field aperture. The method of using a focusing system for observing a diffraction pattern is the same as that in observing a sample image in an ordinary case, and in a case of observing an image of the sample, the image of the sample is focused by making a condition of using any of lenses belonging to the focusing optical system as a weak excitation. FIG. 4 and FIG. 5 show the two optical systems. FIG. 4 shows an observation optical system of the Foucault image of the sample, and FIG. 5 shows an observation optical system of a diffraction pattern of the sample. Further, the diffraction pattern observation optical system is an optical system which is effective for observing the small angle diffraction observation. A description will be given later also concerning the optical system.

In the lens-less Foucault method, as shown in FIG. 4, the crossovers (11, 13) are made to coincide with a position of a selected area aperture 65 by the irradiating optical system 4. As a result, a position of the selected area aperture 65 becomes a diffraction pattern observation position of the sample 3, that is, an inverse space and the selected area aperture 65 can be utilized as an angle restricting aperture as in the objective aperture 65. Inherently, the irradiating optical system is based on an operation independent from the focusing optical system with an object of controlling an irradiating range of the electron beam irradiating the sample and angle spreading of the irradiating electron beam. However, in the lens-less Foucault optical system, the irradiating optical system has a role of forming the crossover at a strictly determined position at a lower portion of the sample, and can be considered as an optical system contributing an operation of irradiating the optical system to the focusing optical system.

When the image of the sample is observed, as shown in FIG. 4, the image is focused by a first imaging lens 61 below the objective lens 5. An operation of the first imaging lens is a contraction focusing similar to that in observing a fluxoid quantum. An expansion image is obtained by a focusing system at and after the second imaging lens, and a maximum amplification becomes about 10,000 times amplification by a four-stage focusing optical system (three imaging lenses+one projecting lens). In order to arrange the selected area aperture at a pertinent position in the electron diffraction pattern as an angle restricting aperture, it is necessary to observe in a state of expanding a diffraction pattern, that is, by a large camera length.

FIG. 5 shows an optical system in observing a diffraction pattern. In comparison with the optical system when an image of the sample of FIG. 4 is observed, this is an optical system strongly exciting the first imaging lens 61, and expanding a position of the selected area aperture 65 to propagate to a focusing system at and after the second imaging lens. A distance from a position of the sample 3 to a position of the selected area aperture 65 corresponds to a camera length obtained by directly propagating the electron beam. The distance is about 100 through 200 mm in an ordinary transmission electron microscope, it is easy to expand the distance by a focusing optical system at a later stage (about 10,000 times), and therefore, as a result, a large camera length of a kilometer order can be obtained. The value is a value 1,000 to 10,000 times larger than a camera length of a conventional transmission electron microscope. That is, the lens-less Foucault optical system is an optical system which is effective also for the small angle electron diffraction pattern observation.

Incidentally, since the irradiating optical system is used for the focusing operation, there is brought about a restriction in a degree of freedom of an area of irradiating the sample. As the simplest method as a countermeasure thereagainst, a pertinent size of an aperture 45 in the irradiating optical system is selected and used. In a case of needing further detailed operation, an irradiation aperture 44 for STEM can be utilized for a microscope in which an object aperture 55 or a scanning electron microscope (STEM) mode is prepared. FIGS. 4 and 5 describe the respective apertures. A description will be given of methods of utilizing the apertures in the following embodiments.

Further, although it is general that the optical system is configured by plural electron lenses, when the electron lens system is adequately adjusted, an irradiation area and an irradiation angle of an electron beam to the sample can continuously be changed. Further, concerning a visual field restriction to the focusing optical system when a diffraction pattern is observed (caution is required since this is not an irradiation region), a conventional objective aperture can be substituted therefor.

First Embodiment

The present invention relates to a method of realizing a Foucault method in a general use type transmission electron microscope which does not include an attachment device for observing a magnetic domain structure (for example, a magnetic shielding lens or the like), and it is a method in which in place of the objective lens turning off a current for excluding an influence of a magnetic field on a sample, a crossover is focused at a selected area aperture position by an irradiating optical system, an electron beam receiving a magnetic deflection is selected to adopt or abandon by the aperture, and focused and observed as a Foucault image by a focusing optical system at a later stage. A small angle diffraction pattern observation of the electron beam receiving the deflection and the Foucault image observation are realized by changing a focal length of the first imaging lens below the objective lens, and a deviation of an optical axis at this occasion is corrected by a deflector below the first imaging lens.

Figure 6:
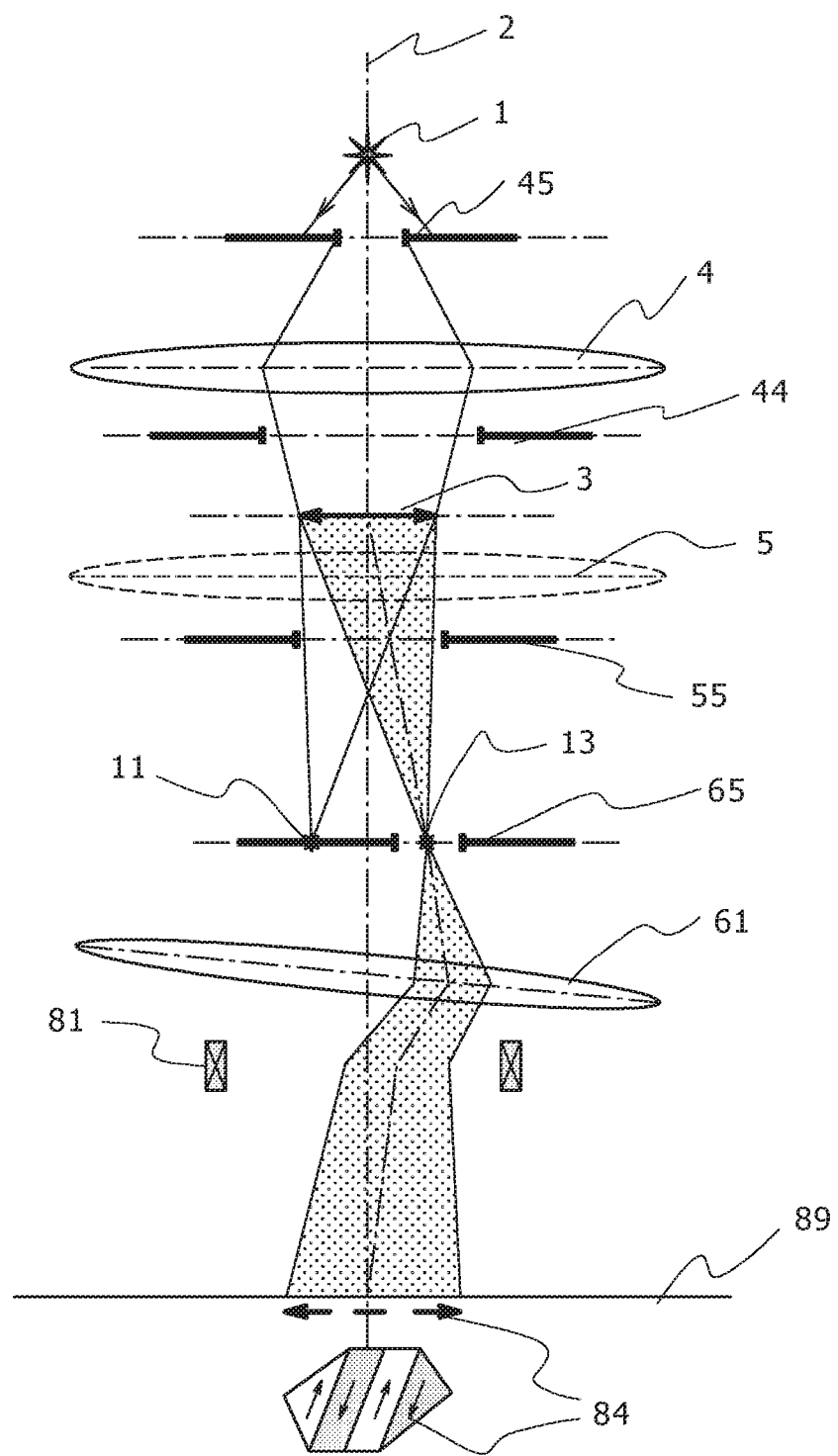
FIG. 6 is a schematic view showing to introduce a deflector below a first imaging lens in a lens-less Foucault method.

FIG. 6 shows a representative optical system of the present invention as the first embodiment. Although FIG. 6 is a view showing a less-less Foucault optical system similar to that of FIG. 4, the view shows a behavior of including a deflector 81 below the first imaging lens 61, and a deviation of the electron beam transmitting the first imaging lens 61 is corrected by the deflector 81. Although the first imaging lens 61 is inclinedly drawn for emphasizing that the first imaging lens 61 is deviated from the optical axis, actually, the first imaging lens 61 is not mechanically inclined in this way.

Also, although in FIG. 6, the deflector is drawn as a small coil, this is due to a convenience of a drawing, the deflector is configured by plural coils wound around a magnetic substance in a shape of a concentric tube with the optical axis as an axis thereof, to knit with the magnetic substance with an optical axis as an axis similarly to a conventional deflector. Further, the electron beam can be deflected in orthogonal two directions in a plane vertical to the optical axis. That is, the electron beam can be deviated not only in a left and right direction on paper face illustrated in FIG. 6, but also in a paper face vertical direction.

In a general use type electron microscope, above all, a high resolution electron microscope, in adjusting the optical system, the adjustment is executed such that other lens system coincides with the optical axis of the objective lens centering on the optical axis of the objective lens. This is an adjusting method in which a top priority is given to an objective lens influencing the most to an image quality of the sample such as a spherical aberration, and the electron microscope used in the present invention is on the premise that such an adjustment is executed. Therefore, in a case of making the objective lens off, the deflector is arranged below the first imaging lens such that the optical axis adjustment giving a priority to the first imaging lens firstly focusing the sample is executed and made to be a center of the optical axis adjustment of the total.

When a system of an electron microscope is configured such that as optical conditions of the Foucault image observation mode of the sample (FIG. 4 or FIG. 6) and the small angle diffraction pattern observation mode of the sample, not only a focal length of the first imaging lens but also conditions of using the deflector (deflection system) in the respective cases are recorded, and can be switched by a simple operation, an operator can observe the Foucault image and the small angle diffraction pattern without receiving a particular load.

Figure 7:
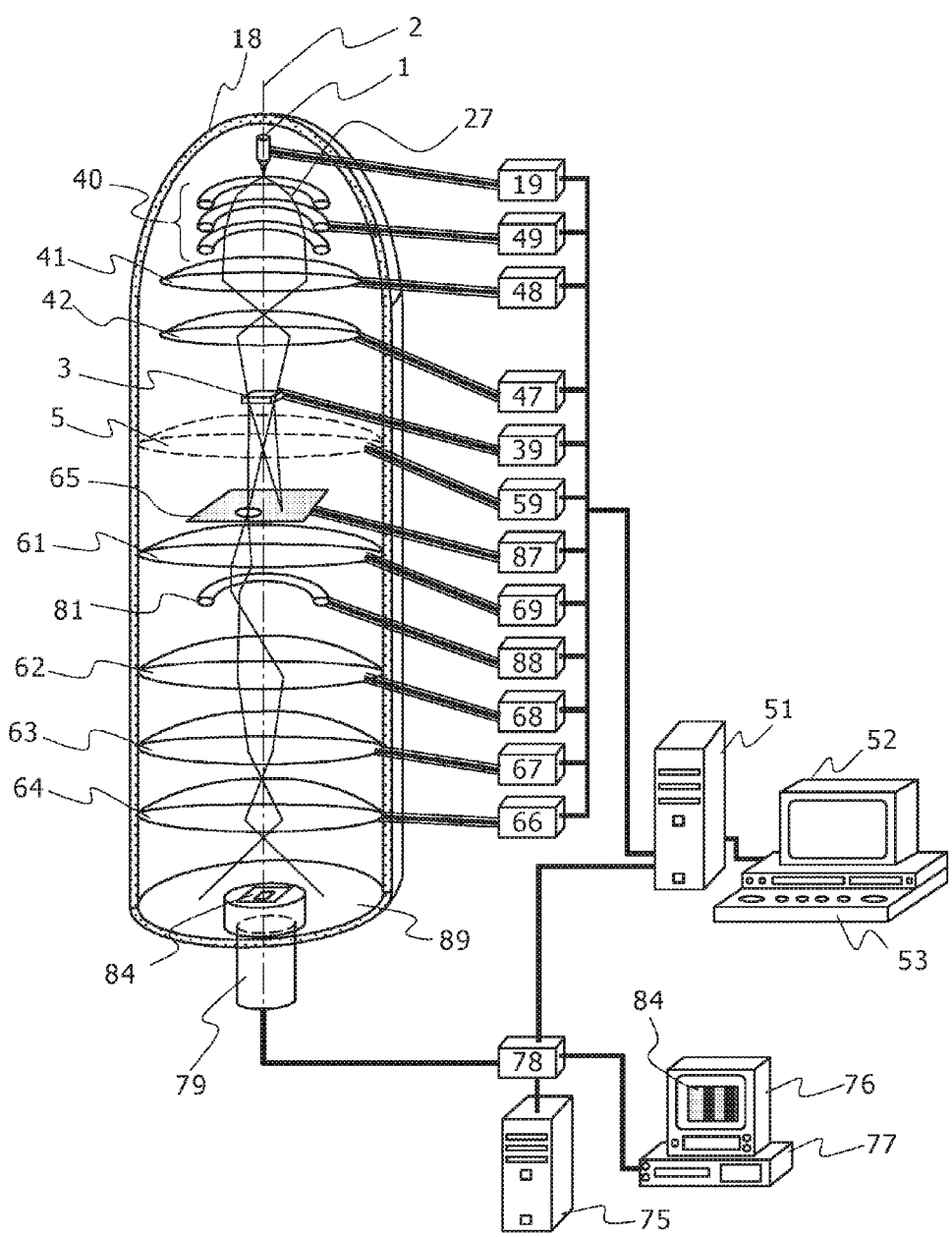
FIG. 7 is a schematic view showing a configuration example of an electron microscope based on the present invention.

FIG. 7 shows a configuration example of an electron microscope having an optical system for executing the present invention. Although FIG. 7 is drawn by assuming a general use type transmission electron microscope having an acceleration voltage of 100 kV through 300 kV, constituent elements of the electron microscope according to the present invention are not limited to those of the figure.

An electron orbit 27 of FIG. 7 is drawn by assuming the Foucault image observation mode. Therefore, the objective lens 5 is made OFF, and is drawn by a broken line to show that the objective lens 5 is made OFF. The electron beam 27 ejected from an electron source 1 is accelerated by a predetermined voltage by an acceleration tube 40, and is irradiated onto the sample 3 by irradiating optical systems (41, 42). For example, according to a normal observation method of the high resolution observation or the like, a crossover (image of light source) is focused on an upper side of the sample, in the lens-less Foucault method, the crossover is focused on a position of the selected area aperture 65 on a lower side of the sample 3. As the sample 3, a magnetic substance having the 180-degree magnetic domain structure is assumed, and a behavior that the crossover is separated to spots is drawn. The deflected electron beam which is selected and extracted in a particular angle range by the restricted view field aperture 65 is transmitted through the first imaging lens 61, thereafter adjusted to propagate on the optical axis 2 by the deflector 81, passes the imaging lens systems (61, 63, 64) at a later stage and focuses the Foucault image 84 at the observing and recording face 89. Incidentally, an aperture of the irradiating optical system, an objective aperture, an irradiation aperture for STEM and the like are not drawn. An explanation will be given thereof respectively at later embodiments.

The Foucault image 84 focused onto the observing and recording face 89 is acquired as an image data by passing an observation record medium 79 of a TV camera or a CCD camera, sent to an arithmetic processing unit 75 via the control unit 78 and outputted to the image display device 76. The image data before and after the processing are recorded to, for example, an image recording device 77. However, the present application is not limited to the configuration. Further, although as the observation recording medium 79, a photograph film for the electron microscope can also be used, in this case, a digitizing process of image data is separately needed. In recent years, the TV camera and the CCD camera become general, and therefore, an explanation has been given by assuming the TV camera or the CCD camera, but handling of the image data is not limited to the configuration of FIG. 7.

In FIG. 7, a control unit 19 of an electron gun, a control unit 49 of an acceleration tube, a control unit 48 of a first irradiating lens, a control unit 47 of a second irradiating lens, a control unit 39 of an inching mechanism or the like of a sample, a control unit 59 of an objective lens, a control unit 87 of a restricted view field aperture, a control unit 69 of a first imaging lens, a control unit 88 of a deflector, a control unit 68 of a second imaging lens, a control unit 67 of a third imaging lens, a control unit 66 of a projecting lens, an observing and recording face 89, an observing and recording medium 79, a control unit 78 of an observing and recording medium, an image recording device 77, an image display device 76, a control system computer 51 of an entire electron microscope device, a monitor 52 of a control system, a control panel 53 of a control system are drawn. However, an electron microscope device and system are not limited thereto.

Further, in an actual device, a deflecting system for adjusting a progressing direction of an electron beam, an aperture mechanism for restricting a transmitting area of an electron beam and the like are present other than constituent elements shown in FIG. 7. However, these devices are omitted in FIG. 7 because the devices have no direct relationship with the present invention. Further, an electron optics system of FIG. 7 is integrated in a vacuum vessel 18, and is continuously exhausted by a vacuum pump. However, a vacuum exhausting system is omitted since the vacuum exhausting system has no direct relationship with the present invention. The same goes with the omission for any drawings of the present application as necessary.

Second Embodiment

Figure 8:
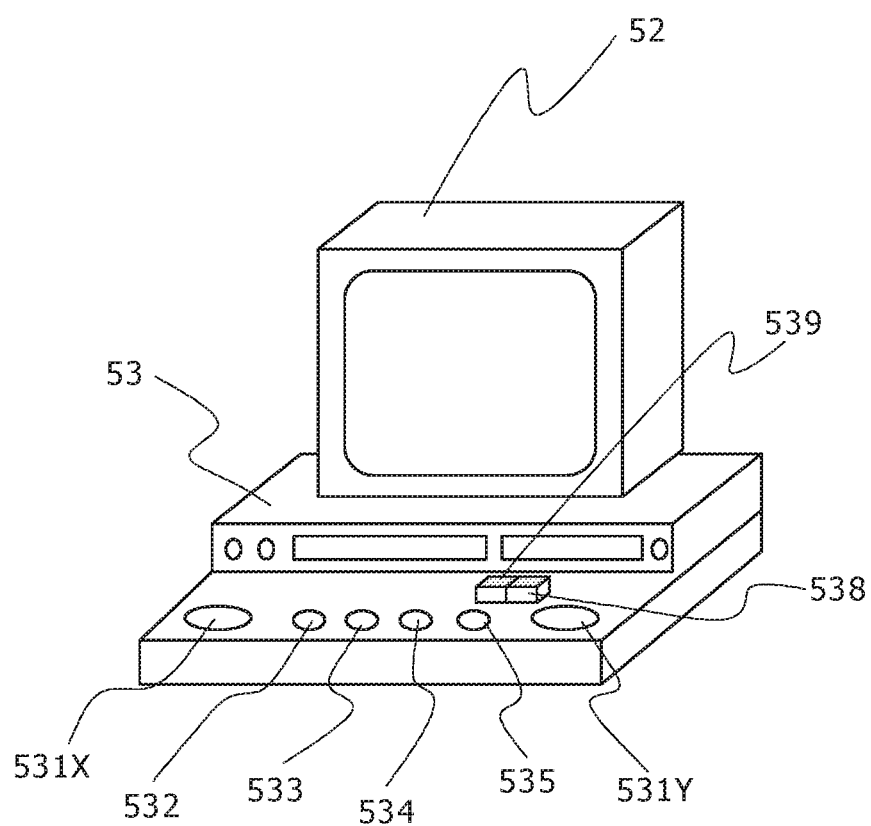
FIG. 8 is a schematic view showing an example of a control panel of an electron microscope based on the present invention.

FIG. 8 shows an example of a control panel of a control system used in the present invention. Ordinarily, a sample inching knob (horizontal two directions of X direction and Y direction: 531X, 531Y), an amplification adjusting knob 532, an irradiating area adjusting knob 533, an irradiating system deflection adjusting knob 534, a focus adjusting knob 535 and the like are arranged on the control panel 53. These are often used in operating an electron microscope, and even in an electron microscope controlled by the control system computer, these are installed on the control panel for reducing a burden of an operation of an operator.

In addition to the knobs or the like described above, the control panel 53 according to the present invention is added with adjustment stopping means 539 of the irradiating optical system and stop release operating means 538 thereof. In the lens-less Foucault method, as described above, crossovers need to be focused at a position of a aperture on a lower side of a sample (in a conventional electron microscope, restricted view field aperture) by using the irradiating optical system. Therefore, after confirming a condition of a focusing optical system, the irradiating optical system needs to fix a condition similarly to the focusing optical system and should not change the condition. However, in an ordinary electron microscope, as described above, the irradiating optical system can be operated independently from and with a priority over other operation for adjusting an irradiating area, an irradiating angle or the like of an electron beam irradiated to a sample. Therefore, in the lens-less Foucault method, what frequently happens is that after confirming the condition of the focusing optical system, the irradiating optical system is erroneously operated, and readjustment of the entire optical system needs to be carried out.

Hence, in order to prevent the erroneous operation described above, there is provided means for stopping to change the irradiating optical system and restarting an adjustment of the stopped irradiating optical system in a successive operation by a simple operation. Thereby, the electron beam operator can execute an observation by the lens-less Foucault method without any particular burden. Incidentally, although in FIG. 8, the adjustment stopping means 539 and the stop release operating means 538 of the irradiating optical system are drawn as the operating portions respectively having shapes of buttons, the present application is not limited to the operating method and the operating portion shape.

Third Embodiment

Figure 9:
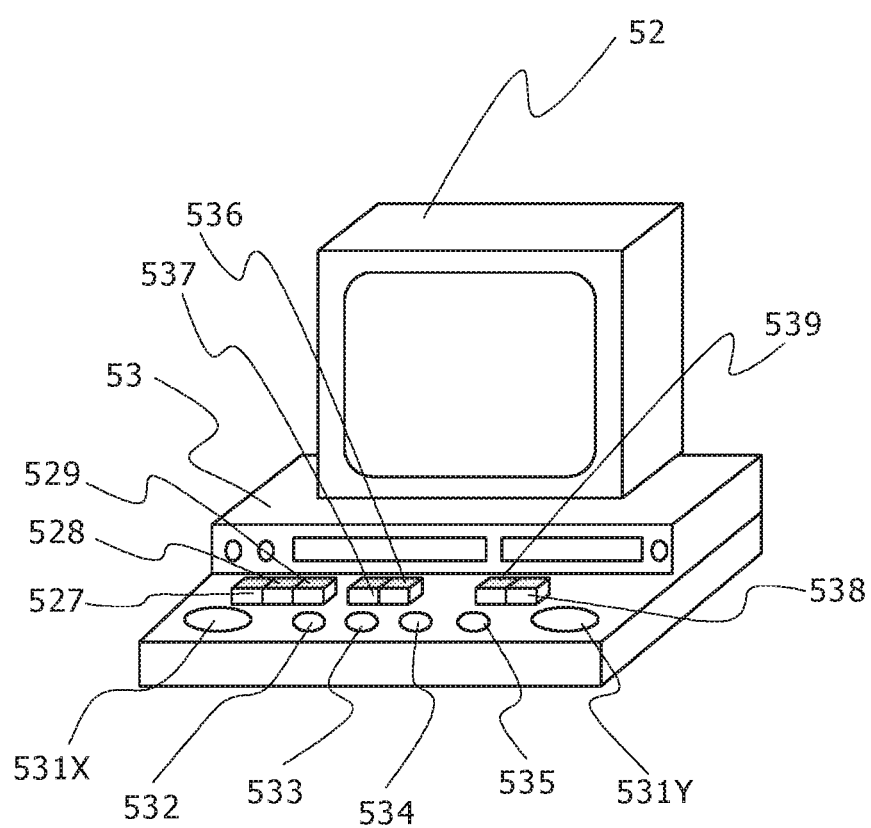
FIG. 9 is a schematic view showing other example of a control panel of an electron microscope based on the present invention.

FIG. 9 shows an example of the control panel 53 of the control system used in the present invention which is different from that of the second embodiment. A shape of the control panel 53, the control knobs and the like including the adjustment stopping means 539 and the stop release operating means 538 of the irradiating optical system (531X, 531Y, 532, 533, 534, 535) are similar to those of FIG. 8. In addition thereto, in FIG. 9, there is drawn a behavior of adding a switching knob of an observation mode on the control panel 53. On the control panel 53 of a conventional electron microscope, there are provided means (successively, 527, 528, 529) for constructing optical systems in accordance with respective objects of observation such as an image observation mode, a low amplification image observation mode, a diffraction pattern observation mode and the like by a simple operation.

In addition to the knob and the like as described above, in the control panel 53 of the present invention, means 536 for constructing an optical system for the Foucault image observation mode in the lens-less Foucault method and means 537 for constructing the optical system of the small angle diffraction pattern observation mode are added. By these means, for example, the two optical systems of FIG. 4 and FIG. 5 can be switched by a simple operation. At this occasion, in the respective modes, a propagation of an electron beam is naturally adjusted by a deflector to be along the optical axis.

An electron microscope operator can execute an observation by the lens-less Foucault method without particular burden by installing switching means of the Foucault image observation mode and the small angle diffraction pattern observation mode. Incidentally, although in FIG. 9, means 536 for constructing an optical system for the Foucault image observation mode and means 537 for constructing an optical system for the small angle diffraction pattern observation mode are respectively drawn as operating portions having shapes of buttons, the present application is not limited to the operating method and the operating portion shape.

Fourth Embodiment

Figure 10:
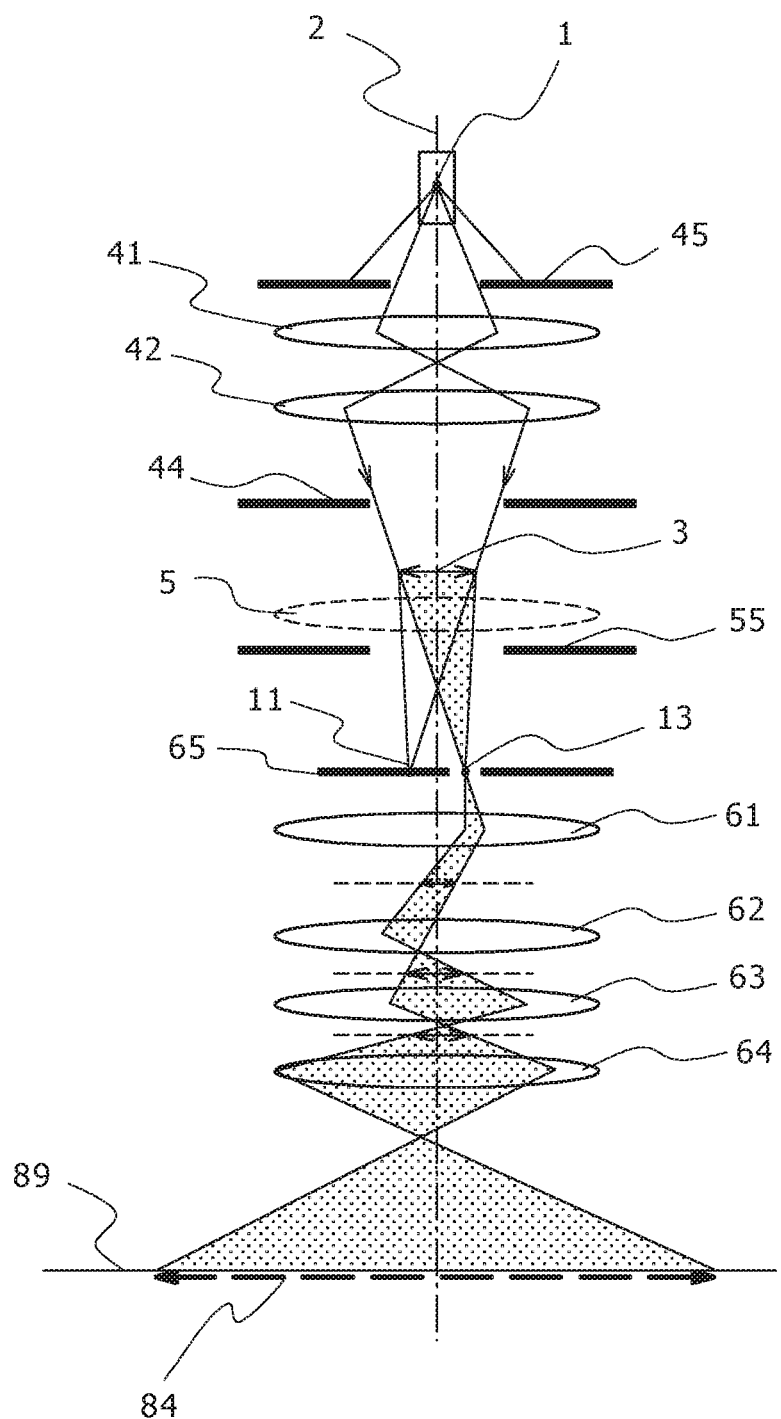
FIG. 10 is a view showing an optical system of an entire electron microscope observing a Foucault image of the present invention.
Figure 11:
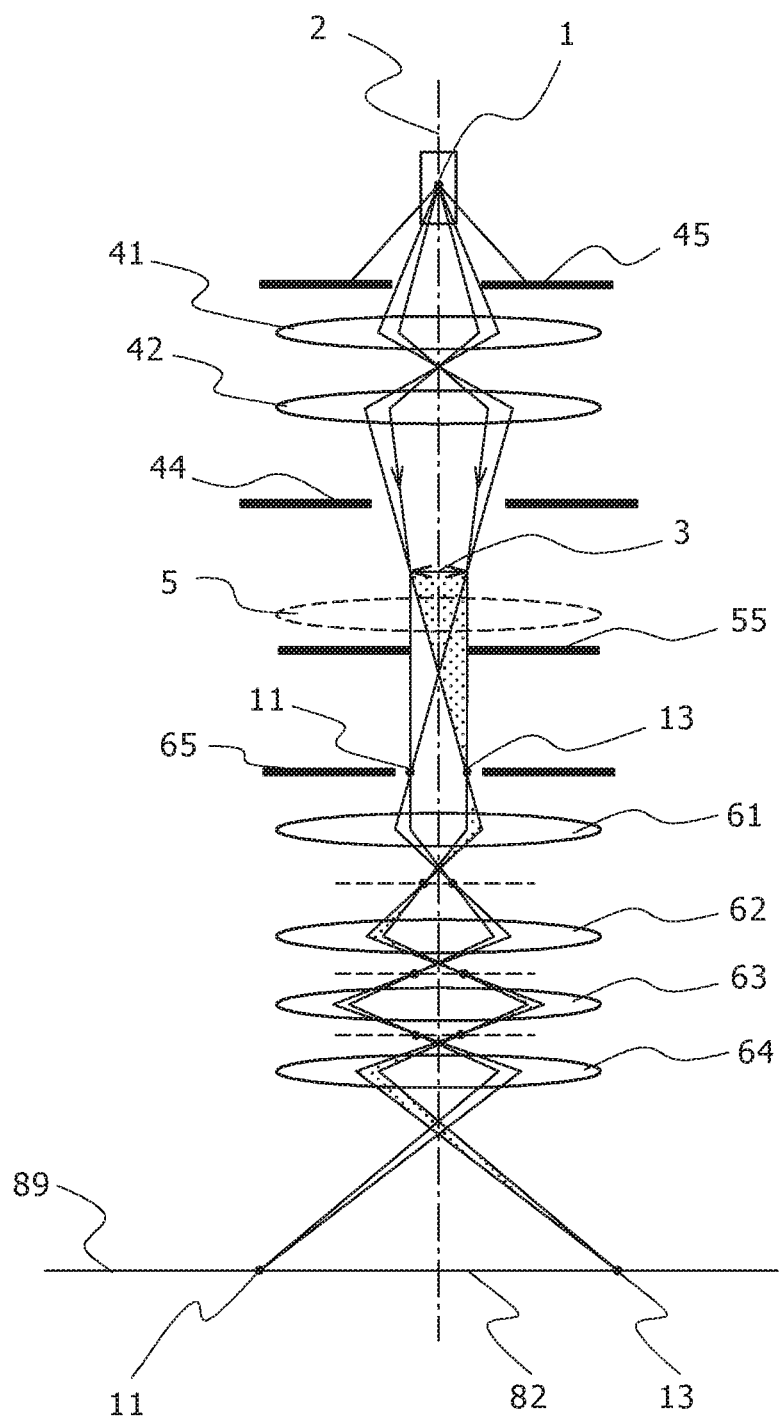
FIG. 11 is a view showing an optical system of an entire electron microscope observing a small angle diffraction pattern of the present invention.

FIG. 10 shows an optical system of an entire electron microscope which becomes an example of the Foucault image observation mode, and FIG. 11 shows an optical system of an entire electron microscope which becomes an example of the small angle diffraction pattern observation mode, respectively. Although upper sides of the first imaging lens 61 of FIG. 10 and FIG. 11 are respectively similar to those of FIG. 4 and FIG. 5, in FIG. 10 and FIG. 11, electron lenses (62, 63, 64) at a later stage of the second imaging lens 62, a aperture 45 of an irradiating optical system, an irradiating aperture 44 for STEM, an objective aperture 55, and a restricted view field aperture 65 are clearly described. The switching of the optical system by switching the mode described in the third embodiment corresponds to switching of FIG. 10 and FIG. 11.

In switching the modes described above, in the Foucault image observation mode, there is arbitrariness in selecting an amplification of an image, and there is arbitrariness in selecting a camera length in the small angle diffraction pattern observation mode. That is, whereas a lens mainly in charge of switching of modes is the first imaging lens, a lens mainly in charge of an amplification of a camera length is the third imaging lens, and therefore, in switching the modes, what needs to determine is how amplification and the camera length are selected, that is, a condition of the third imaging lens. Therefore, in the present invention, the operation is controlled such that the operation returns to a final amplification or a final camera length when the mode is observed in a previous time. Further, the operation modifies the amplification and the camera length to values suitable for the observation state at that occasion newly from the returned original state. An observation condition desired by an operator is reached finally by repeating such operation.

The respective lens conditions and the operation condition of the deflector in the mode described above are memorized in the computer system computer, and operating conditions at a previous time or the first operating condition can immediately be reproduced as necessary.

Further, although the lens condition and the operating condition of the deflector are frequently controlled by currents flowing to coils of the respective electron lenses and deflectors, as shown in FIG. 10 and FIG. 11, also a position and an aperture diameter of the aperture become important operation conditions in the Foucault method. For example, FIG. 10 and FIG. 11 show a behavior that the aperture 45 of the irradiating optical system determines an electron beam irradiating area to the sample 3. That is, in the mode switching, it is a base of the control that the position and the aperture diameter of the aperture 45 of the irradiating optical system are not changed.

In changing the amplification of the image in the Foucault image observation mode, and in changing the camera length in the small angle diffraction pattern observation mode, not the first imaging lens in charge of the mode change but the other imaging lenses are in charge of the mode change. Mainly, however, the optical system is configured such that the third imaging lens is in charge of the changes. Operating conditions of all the lenses and all the deflectors at the respective magnifications and the respective camera lengths are memorized, and the optical system may be constructed by reading the corresponding lens data and the like in the respective cases, in a case where the sample is switched or the observation azimuth is changed by inclining the sample, the operation of the sample is shifted from the condition memorized beforehand. The shift is finely adjusted by the first imaging lens in the operating stage of adjusting the optical system first. Therefore, the lens condition, that is, the focal length of the first imaging lens is not changed even in changing the amplification by the third imaging lens or changing the camera length as described above. Although the condition of the first imaging lens needs to modify in accordance with the change of the lens condition of the other imaging lens such as the third imaging lens, this is determined to be a small amount, and therefore, the focal point distance of the first imaging lens is not changed even in a case where the focal length of the other imaging lens of the third imaging lens or the like is changed.

Fifth Embodiment

For example, the focus adjusting knobs on the control panel shown in FIG. 8 and FIG. 9 are the knobs in charge of adjusting the focus of the image of the sample and adjusting the focus of the diffraction pattern of the sample, and the actually controlling electron lens differs by mode. For example, although in the image observation mode, the focal length distance of the objective lens is changed, in the low amplification image observation mode, the focal length of the first imaging lens or the second imaging lens (depending on optical system) is changed, and in the diffraction pattern observation mode, the focal length of the first imaging lens is changed. This is because of a control panel using method signifying "focus adjustment for an object which is looked at", and the electron microscope operator can execute an adjustment concentratedly only on an object which is looked at (image or diffraction pattern) without being conscious of which lens needs to be adjusted.

Also in the present invention, in the Foucault image observation mode, the first imaging lens is made to be able to be operated and also in the small angle diffraction pattern observation mode, the first imaging lens is made to be able to be operated by the focus adjusting knob. Thereby, also in the lens-less Foucault method, the electron microscope operator can execute an efficient observation experiment with no burden without being conscious of which lens needs to be adjusted.

Sixth Embodiment

FIG. 12, FIG. 13, FIG. 14 and FIG. 15 show use of the device in a case of also using an energy analyzer in the Foucault image observation mode or the small diffraction mode according to the present invention. Although an energy loss spectrograph (EELS) is assumed as the energy analyzer, the method of the present invention can be executed so far as the analyzer can be used along with the transmission electron microscope, and the present application is not limited to the electron energy loss spectrograph (EELS).

Figure 12:
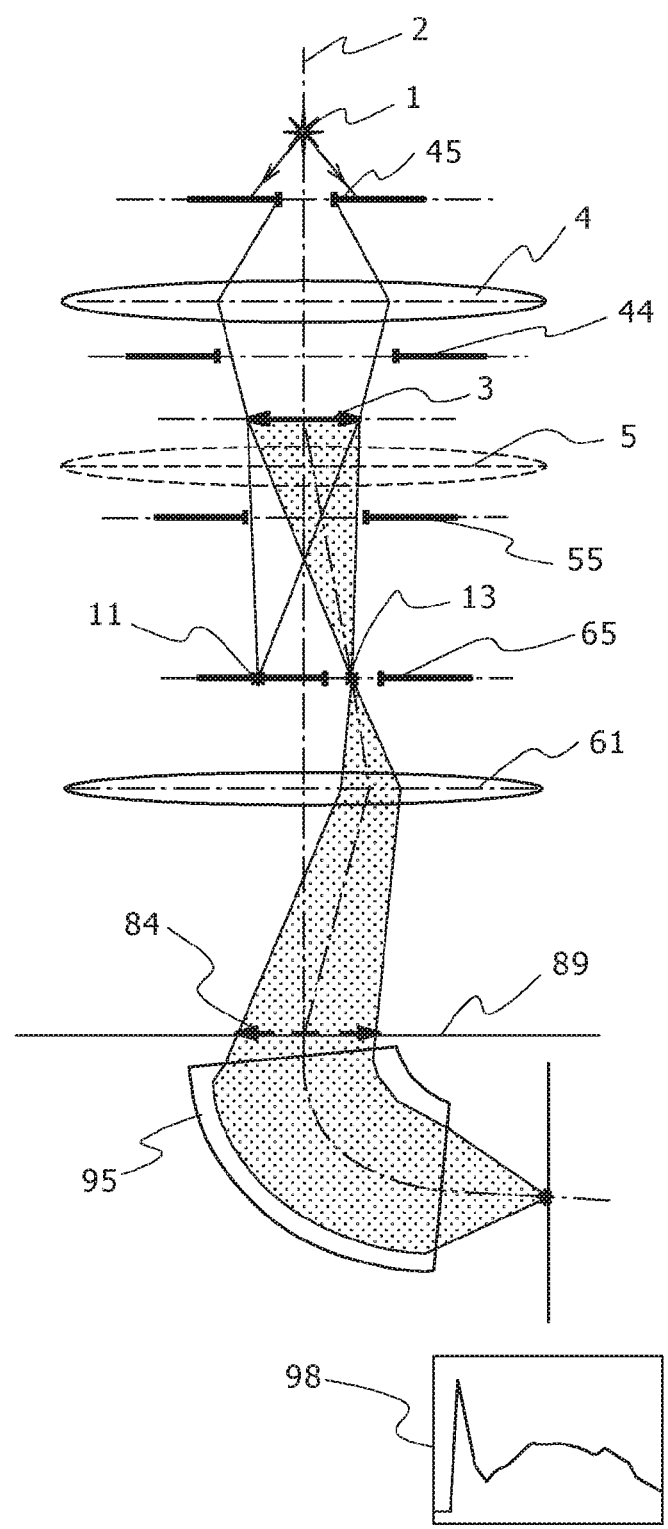
FIG. 12 is a view showing an example of measuring an energy spectrum by also using EELS in a lens-less Foucault method.

FIG. 12 shows a behavior of measuring an energy spectrum 98 of an electron beam by introducing the electron beam focusing the Foucault image 84 to EELS 95. The energy spectrum 98 only by the electron beam having a particular deflection angle is obtained. That is, for example, in a case where a certain element present at a particular magnetic domain having an operation of deflecting an electron beam in a certain determined direction is segregated, the element kind and the fact of segregation can be learned. Spectra for respective magnetic domains can be measured by the method, and knowledge can be obtained concerning a relationship between a magnetic domain structure and an element distribution. FIG. 12 shows an optical system focusing a Foucault image by an electron microscope, and thereafter, introducing the Foucault image to EELS.

Figure 13:
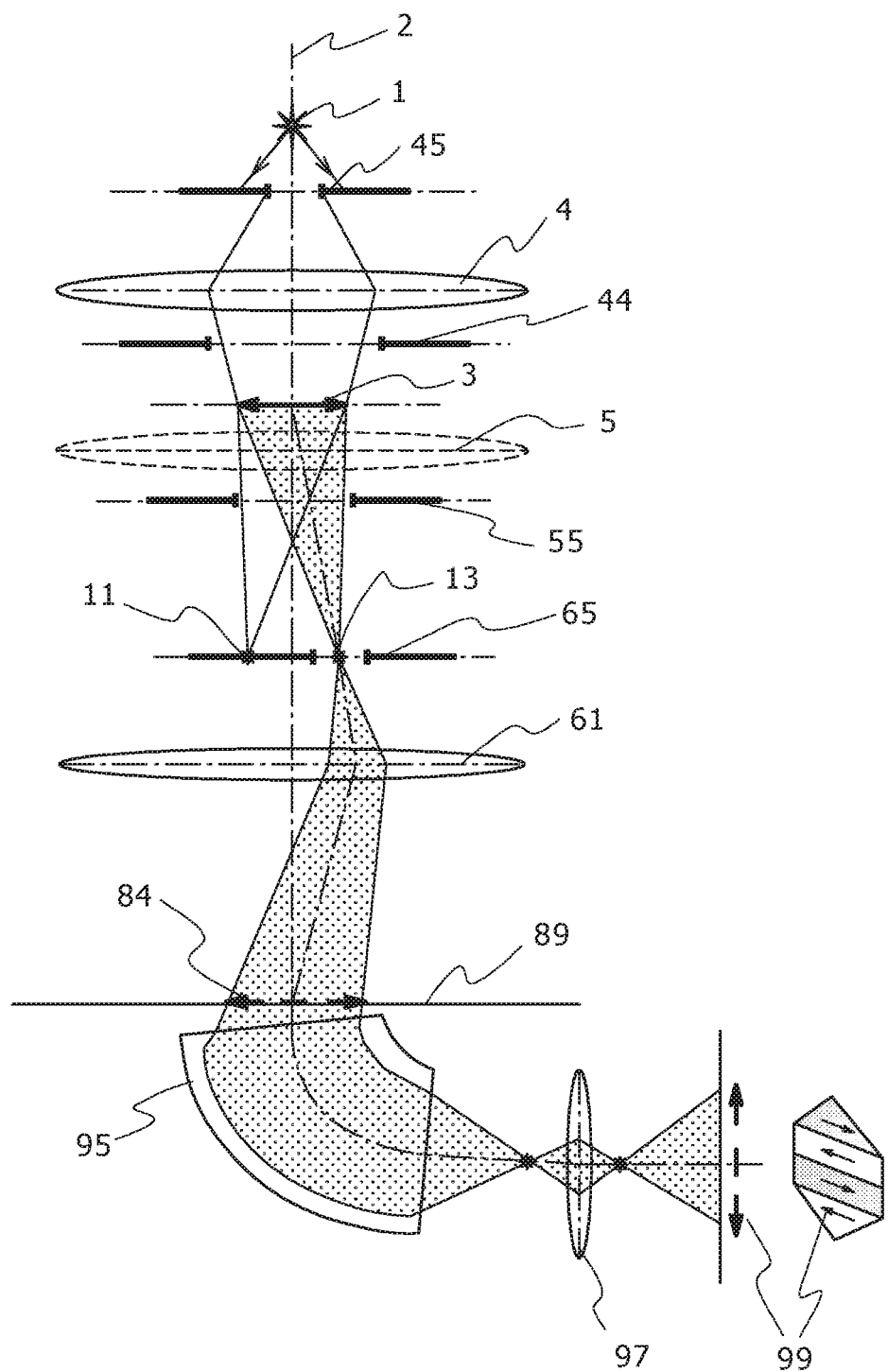
FIG. 13 is a view showing to observe an image by an energy loss electron by also using EELS in a lens-less Foucault method.

Although FIG. 13 is the same as FIG. 12 in that an electron beam focusing the Foucault image 84 is introduced to EELS 95 after focusing the Foucault image 84, this is an example of observing an image 99 by an energy loss electron by using an electron optics system 97 of EELS. In the Foucault optical system, after visualizing the deflection angle of the electron beam, an energy distribution of the electron beam is visualized. That is, not only the magnetic domain structure but a distribution density of the segregated element in the magnetic domain is visualized.

Figure 14:
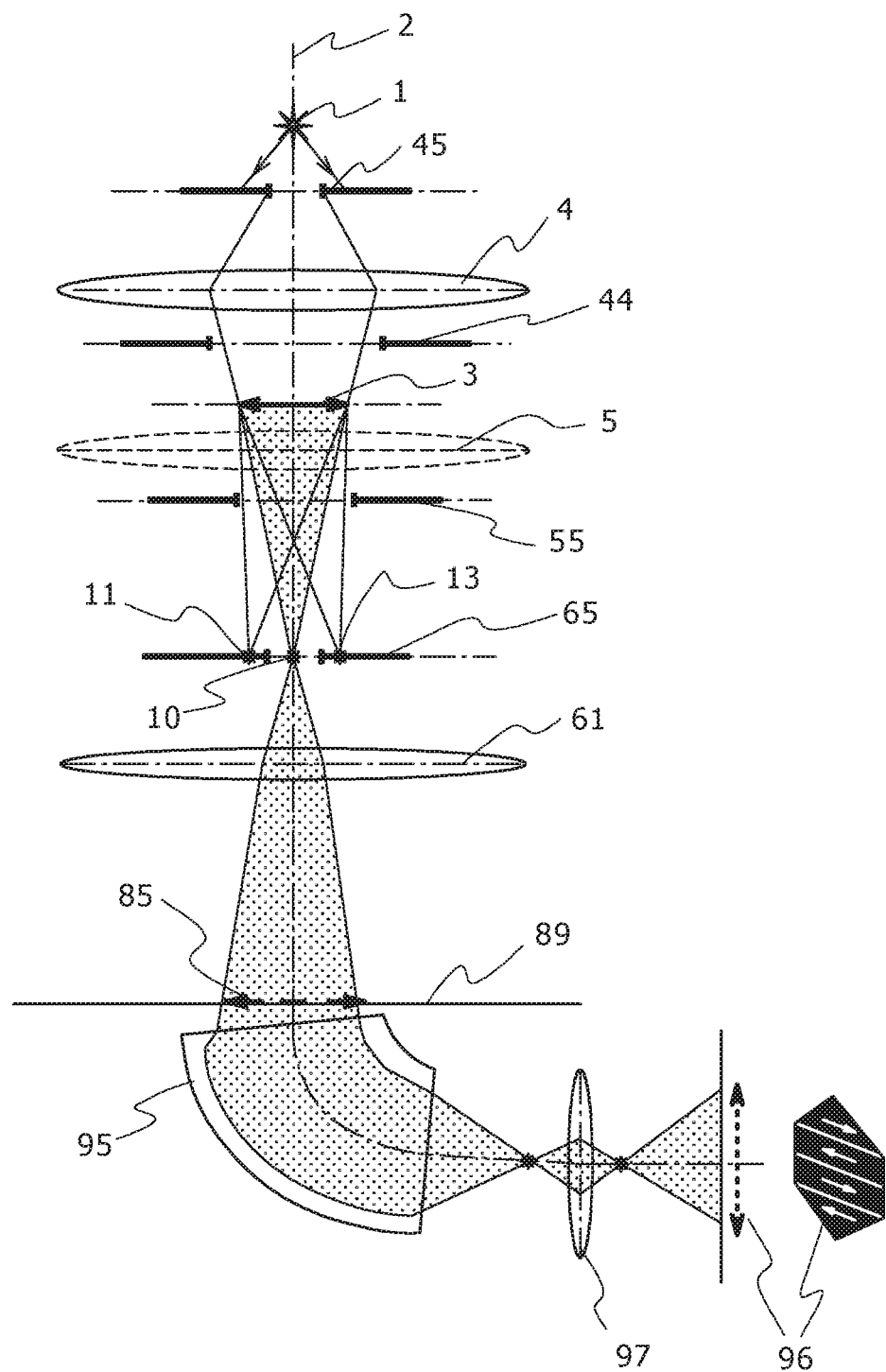
FIG. 14 is a view showing to observe an image by an energy loss electron of an electron beam which does not receive an electromagnetic deflection by both using a lessless Foucault method and EELS.

FIG. 14 shows an example in which an electron beam which does not receive the deflection is focused as the Foucault image 85, thereafter, the electron beam is introduced to EELS 95 and an image 96 by an energy loss electron is observed. For example, in a case where there is a nonmagnetic grain in the sample 3, not only the grain can be identified as the Foucault image 85 but the knowledge concerning the element kind in the grain can be obtained from the energy spectrum 98 as well as the knowledge can be obtained concerning the distribution of a specific element in the nonmagnetic grain from the image 96 by the energy loss electron.

Figure 15:
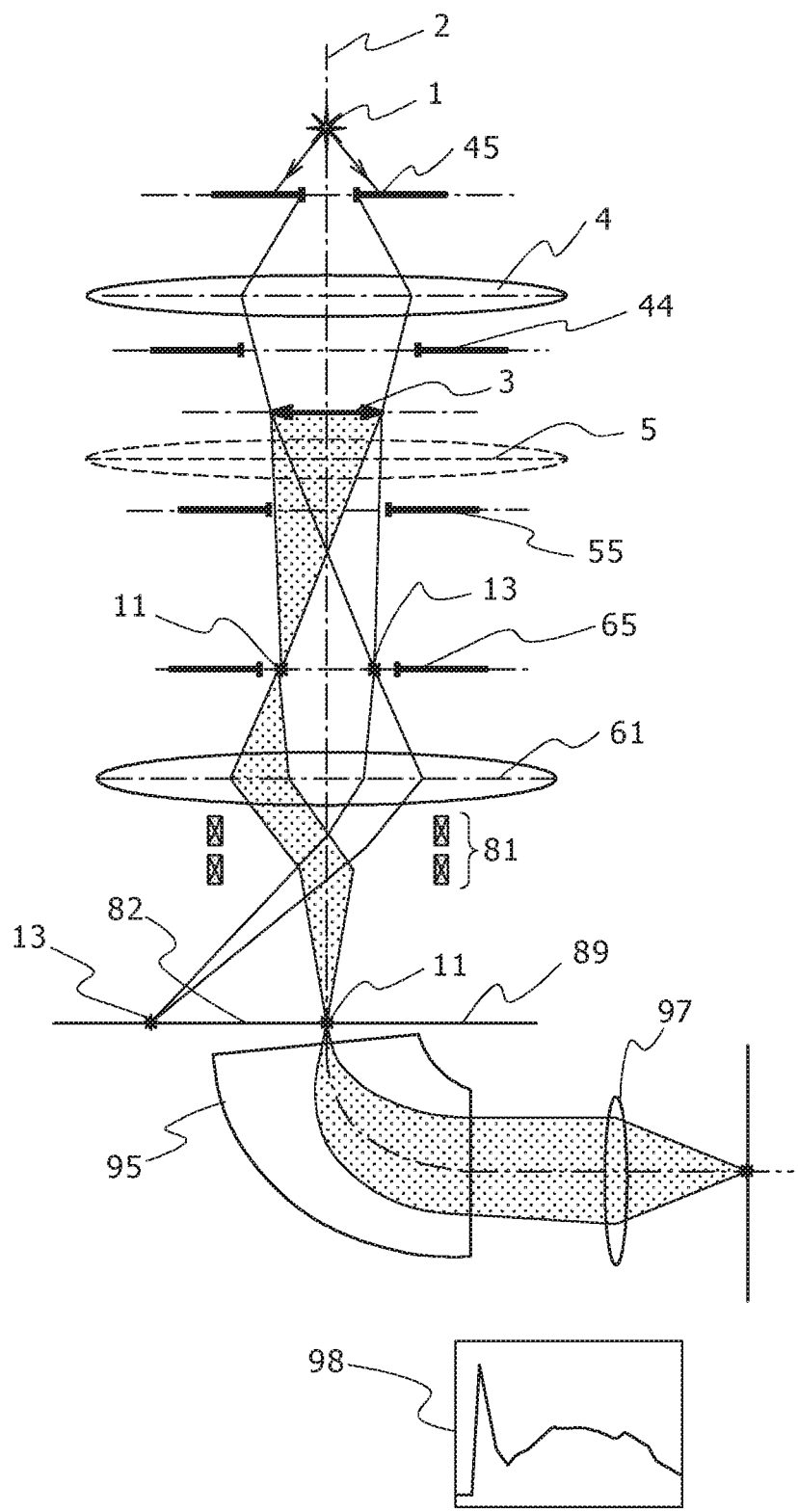
FIG. 15 is a view showing an example of measuring an energy spectrum by both using a small angle diffraction pattern observation method and EELS.

FIG. 15 shows an example in which the small angle diffraction pattern 82 is focused by the electron microscope, thereafter, a particular diffraction spot (crossover 11 in FIG. 15) is introduced to EELS 95. Although in FIG. 15, the energy spectrum 98 is drawn as an example of measuring, the image 99 by the energy loss electron can also be observed by a way of using the electron optics system 97 of EELS. The knowledge and the characteristic obtained are similar to those described in FIG. 12 through FIG. 14. A behavior of operating the deflector 81 is illustrated for taking the diffraction spots (11, 13 and the like) in the diffraction pattern 82 to EELS 95. Incidentally, although the deflector 81 having a two-stage structure different from that of FIG. 6 is exemplified, the present application is not limited thereto.

As described above, use of both of the lens-less Foucault method of the energy analyzer explained from FIG. 12 through FIG. 15 differs in a method of combining the optical system used by an object intended to observe and measure and the deflection angle distribution at that occasion. An experiment having an optimum combination may be executed in accordance with an experimental condition.

Seventh Embodiment

Figure 16:
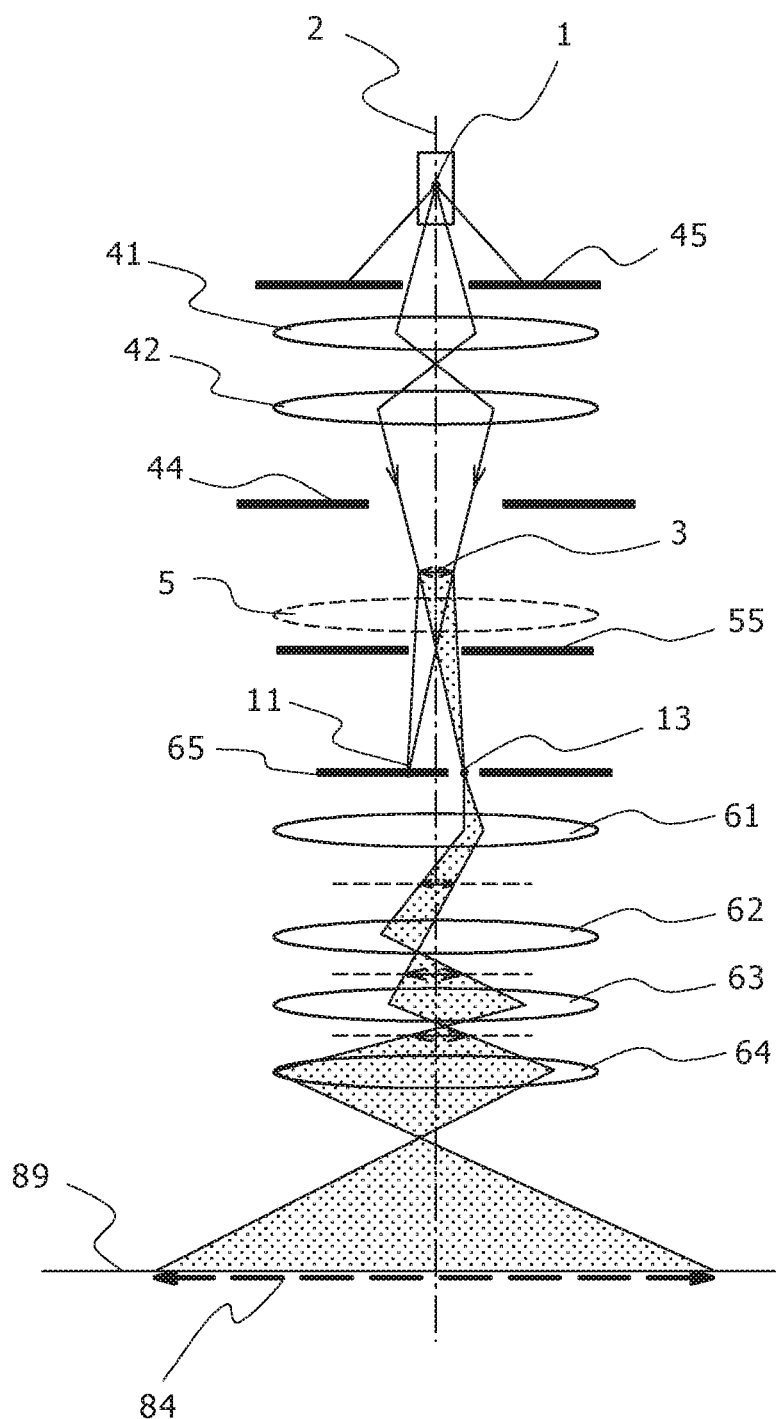
FIG. 16 is a view showing an example of an optical system restricting a space range of an electron beam in which an objective aperture contributes to focusing.

FIG. 16 shows an example of an optical system of an entire electron microscope which differs from FIG. 10 of the Foucault image of the observation mode. Although FIG. 16 is the same as FIG. 10 in that an irradiating range of the sample 3 by the electron beam is determined by the aperture 45 of the irradiating optical system, FIG. 16 differs from FIG. 10 in that spatial ranges of electron beams focusing crossovers (11, 13) after transmitting the sample are determined by the objective aperture 55. In a case of FIG. 16, the objective aperture 55 achieves an operation similar to that of the selected area aperture in a case of an ordinary electron microscope. That is, by restricting the spatial ranges of the electron beams introduced to the imaging lens system (61, 62, 63, 64) at a later stage of the sample, for example, use of receiving significantly an influence of aberration, excluding an electron beam in a range which is not necessary to observe previously can be carried out. The space range restriction of the electron beams can be executed quite independently from irradiating the electron beam to the sample 3, and therefore, the sample irradiating condition of the electron beam is not changed. Therefore, the control of the observation condition by changing the objective aperture 55 does not generate a new sample drift or the like.

Eighth Embodiment

Figure 17:
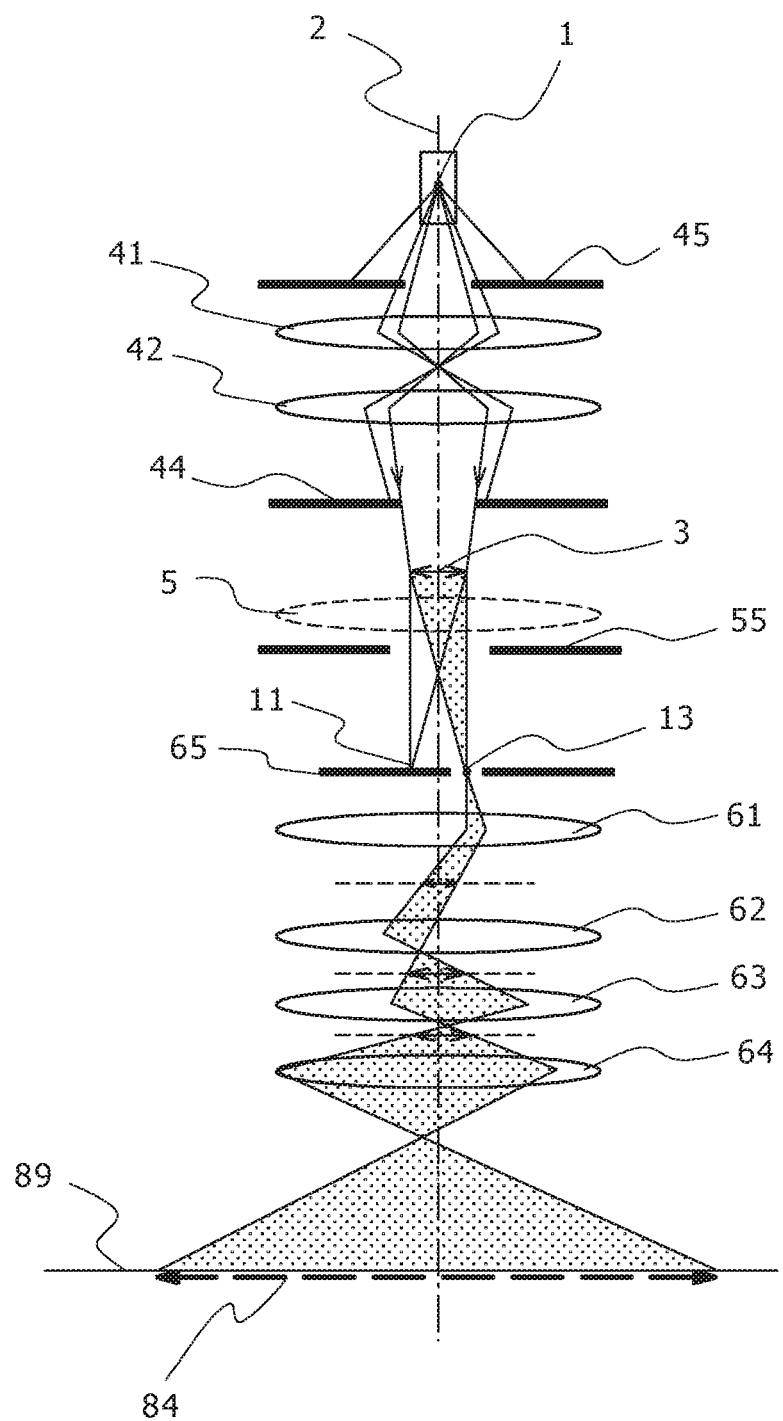
FIG. 17 is a view showing that an irradiation aperture for STEM restricts an amount of an electron beam irradiating a sample.

FIG. 17 shows an example of an optical system of an entire electron microscope which differs from that of FIG. 16. FIG. 17 shows an example of controlling a spatial range of an irradiated electron beam by using an irradiation aperture 44 for STEM disposed between the irradiating optical system (41, 42) and the sample 3 in a transmission electron microscope having an STEM mode. In the irradiation aperture 44 for STEM, an amount and a range of an electron beam irradiating the sample 3 can directly be controlled, and therefore, for example, this is an effective aperture when an irradiation amount of an electron beam is intended to control in the lens-less Foucault method in observing a biological sample. The irradiating range can be changed in details when the aperture 45 of the irradiating is used along therewith.

Ninth Embodiment

In an ordinary case, in electron beam holography, a selected area aperture and an electron beam biprism are frequently used or exchanged for use. That is, also in the present invention, an electron beam biprism can be arranged at a position of focusing the crossover (image of light source) (position of selected area aperture) by the irradiating optical system. Thereby, even in an optical system which does not use an objective lens, the twin Foucault method (Patent Literature 1) (Nonpatent Literature 2) can be executed. Incidentally, electron beam holography and an electron beam biprism are described in Patent Literature 1, Nonpatent Literature 2, and Nonpatent Literature 3.

Figure 18:
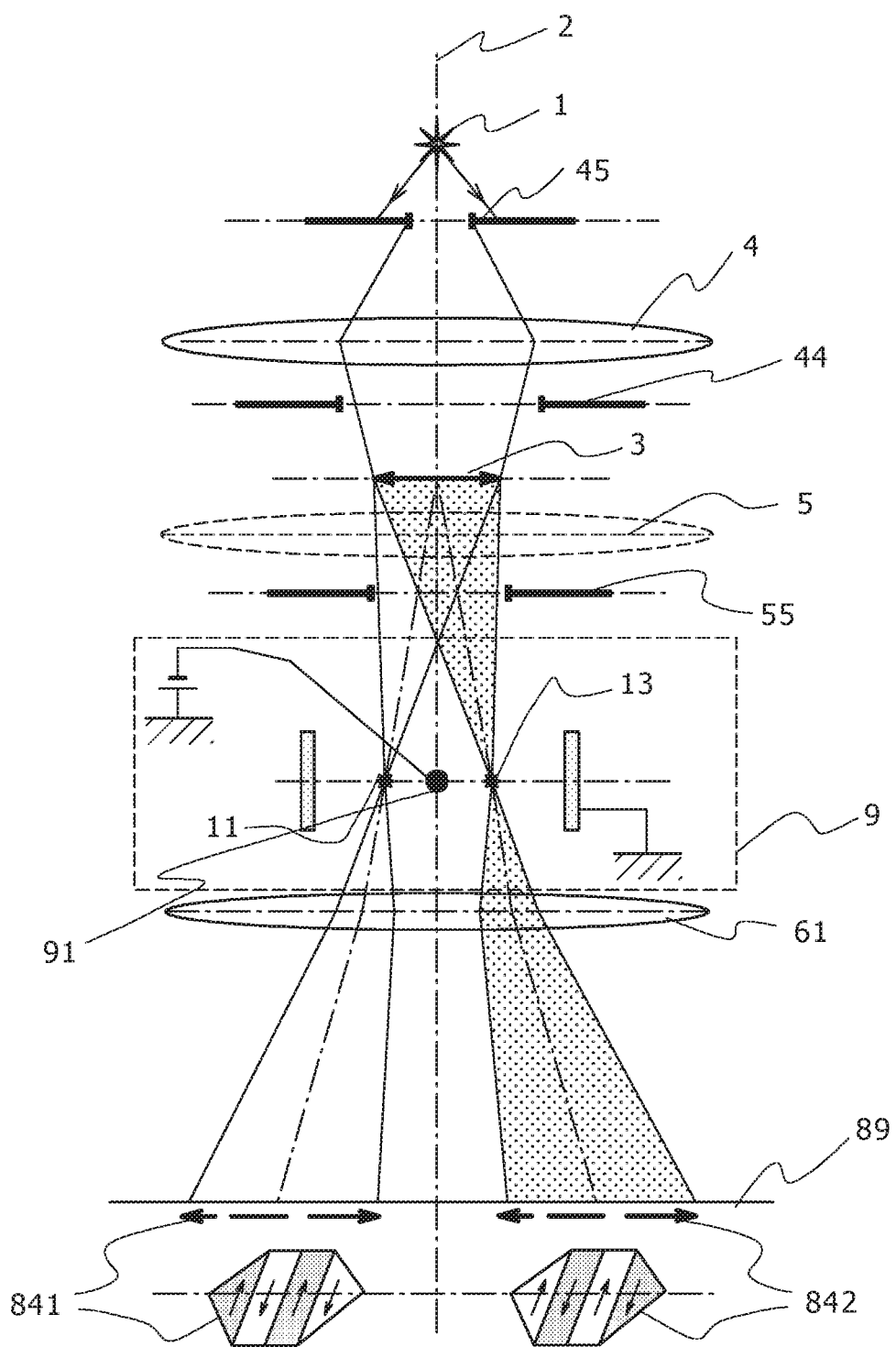
FIG. 18 is a view showing an optical system in a case where a lens-less Foucault method is executed by using an electron beam biprism in place of a selected area aperture.

In the present invention, FIG. 18 shows an optical system in a case of executing a twin Foucault method. This is an optical system in which an electron beam receiving a deflection by transmitting the sample 3 is not selected to be adopted or abandoned, but a deflection is applied or a deflection is restrained further by an electron beam biprism 9, and electron beams receiving deflections respectively by the sample 3 are individually focused at different positions on the observing and recording face 89. That is, the two Foucault images (841, 842) are observed at a time. Although in FIG. 18, as an example, an example of applying a negative voltage to a filament electrode 91 of the electron beam biprism 9 is described, positiveness or negativeness of the applied voltage is not limited. In a case where the positiveness and the negativeness of the applied voltage are inverted, only arrangements of the two Foucault images observed in a left and right direction are switched. Although the twin Foucault method is an observing method based on a new concept of an observation of one mirror two images, the means can also be executed in the present invention.

Tenth Embodiment

A result of an experiment executed concerning the present invention will be described. An electron microscope used is an HF-3300 high resolution transmission electron microscope (acceleration voltage 300 kV) made by Hitachi High Technologies Corporation and is a general use type. FIG. 4 and FIG. 5, or FIG. 6 and FIG. 5 when described by including a deflection system for adjusting an optical axis, were adjusted to be switched by one operation. That is, an image observation mode of a sample and a diffraction pattern observation mode of the sample were adjusted to be switched in one operation with an excellent reproducibility. Further, when an entire electron lens system is described, FIG. 9 and FIG. 10 correspond thereto. A sample subjected to observation is a thin film of a material $La_{0.75}Sr_{0.25}MnO_3$ (LSMO) of a manganese oxide group, and it is known that a twin crystal is configured, and 180-degree conversion magnetic domain structure and 90° magnetic domain structure are configured.

Figure 1:
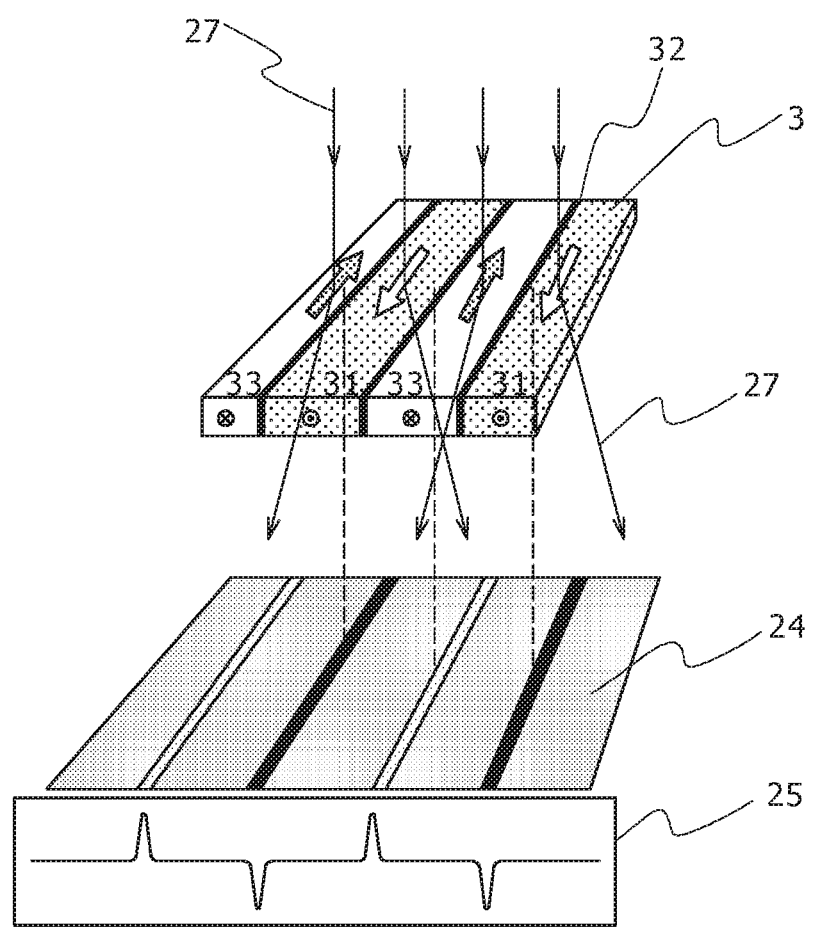
FIG. 1 is a schematic view for explaining a principle of a Lorenz microscope method, particularly, Fresnel method.
Figure 2:
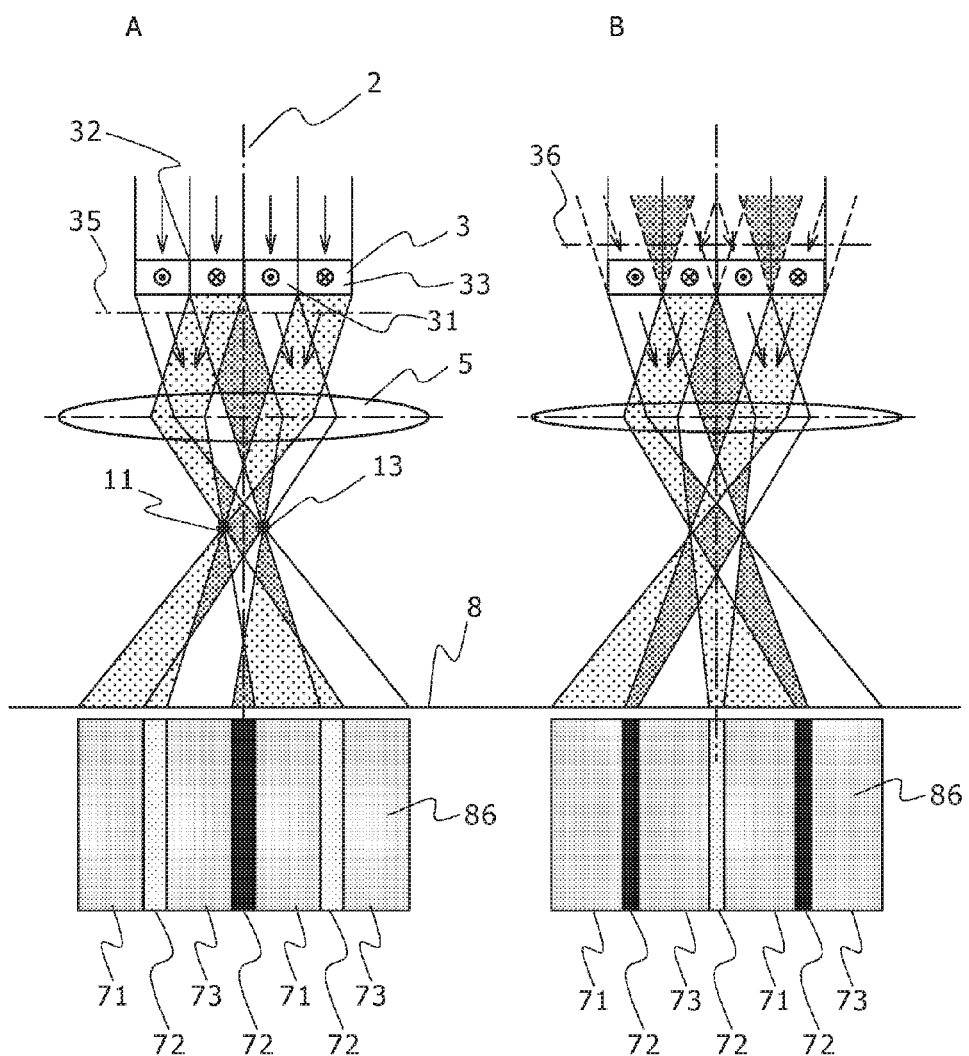
FIG. 2 is a schematic view for explaining a Lorenz microscope method (Fresnel method).
Figure 3:
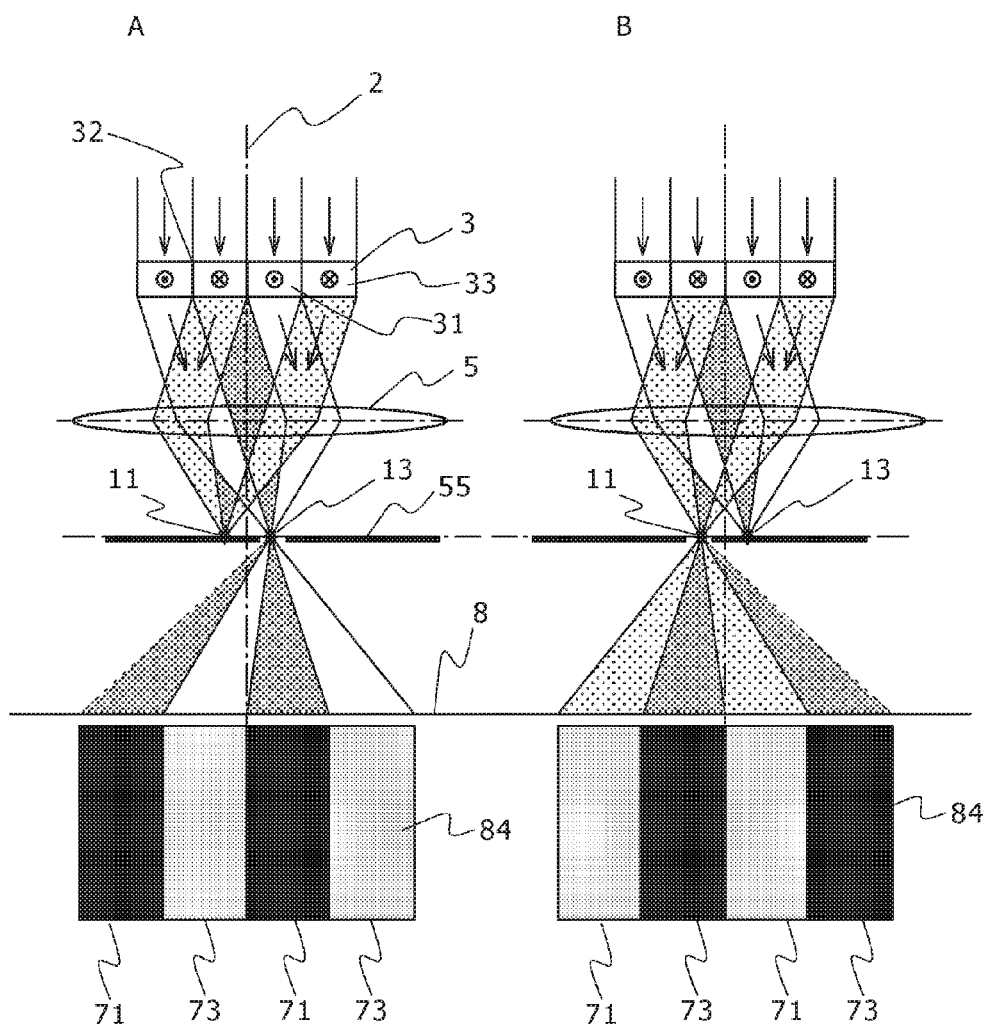
FIG. 3 is a schematic view for explaining a Lorenz microscope method (Foucault method).
Figure 19:
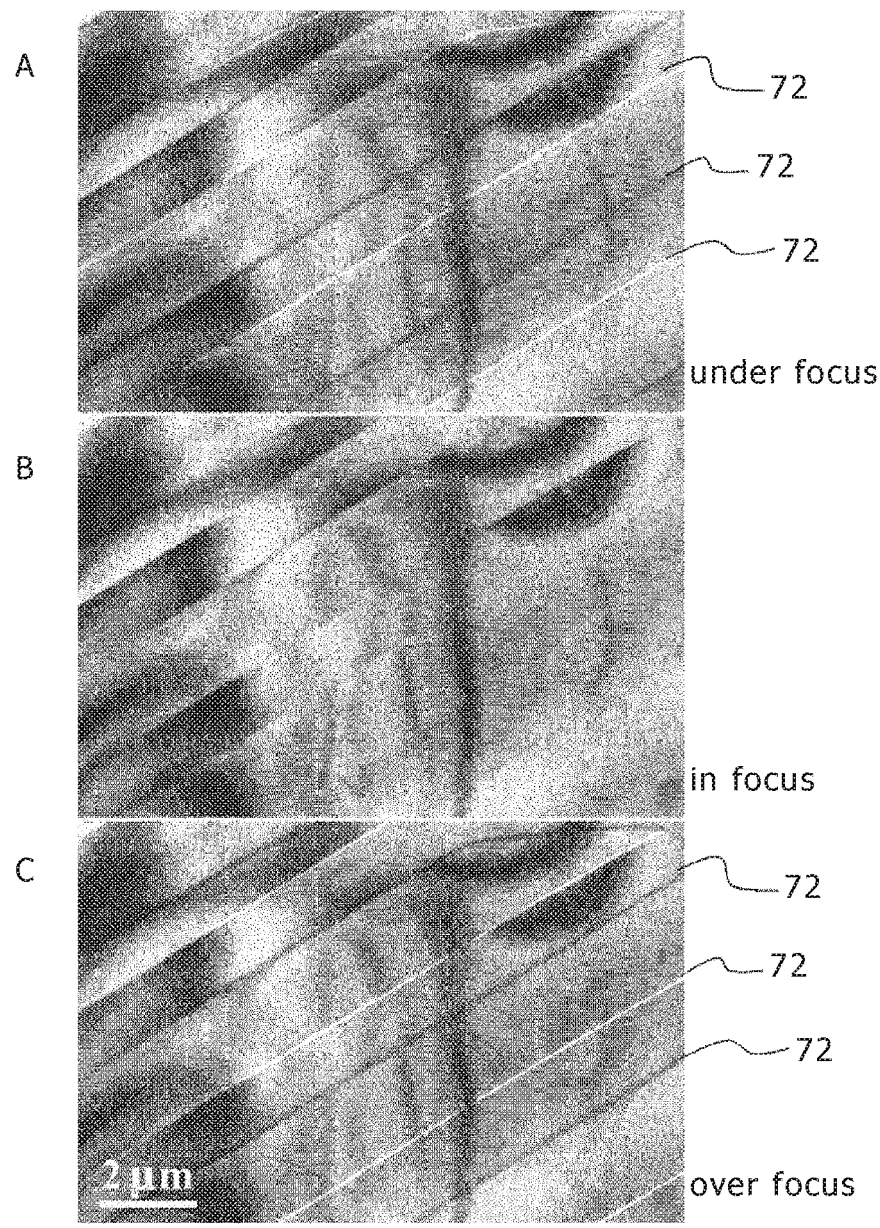
FIG. 19 shows an experimental example of a Fresnel image of a 180-degree magnetic domain structure by a lens-less Foucault method.

FIG. 19 shows a Fresnel image of LSMO. Notation A designates an under focus (deficient focal point) image, notation B designates in focus (regular focal point) image, and notation C designates an over focus (excessive focal point) image. What look like in band-like shapes from upper right over to a left right in the respective drawings are magnetic domains respectively magnetized in inverse directions, and it is known from other knowledge that a range of the observation of the sample is configured by a 180-degree magnetic domain structure. Linear contrasts 72 which are looked at boundary portions of the band-like areas of FIGS. 19A and 19C are magnetic walls. It is learned that the linear contrasts 72 of the same portions are inverted in the under focus image A and the over focus image C. Also, the linear contrasts 72 are inverted also at contiguous boundary portions in FIG. 19A, or in contiguous boundary portions in FIG. 19C. It is learned that the contrast 72 of the Fresnel image of the magnetic wall portion is changed by focusing and an arrangement of magnetic domains. That is, the details have been explained in FIG. 1 and FIG. 2.

Other contrast in FIG. 19, for example, black stripe patterns in a muscle-like shape are observed in an up and down direction at center portions of drawings of A through C in FIG. 19, this is an equally inclined interference pattern, and is a contrast caused by distorting the sample thin film by about Bragg angle in a crystal. Although a break is observed in the equally inclined interference pattern, this shows that the break portion is a boundary of a twin. It is learned from an observation result described above, that the magnetic wall is along the twin boundary. In this way, also in the present invention, the magnetic wall can easily be visualized by the Fresnel method.

Figure 20:
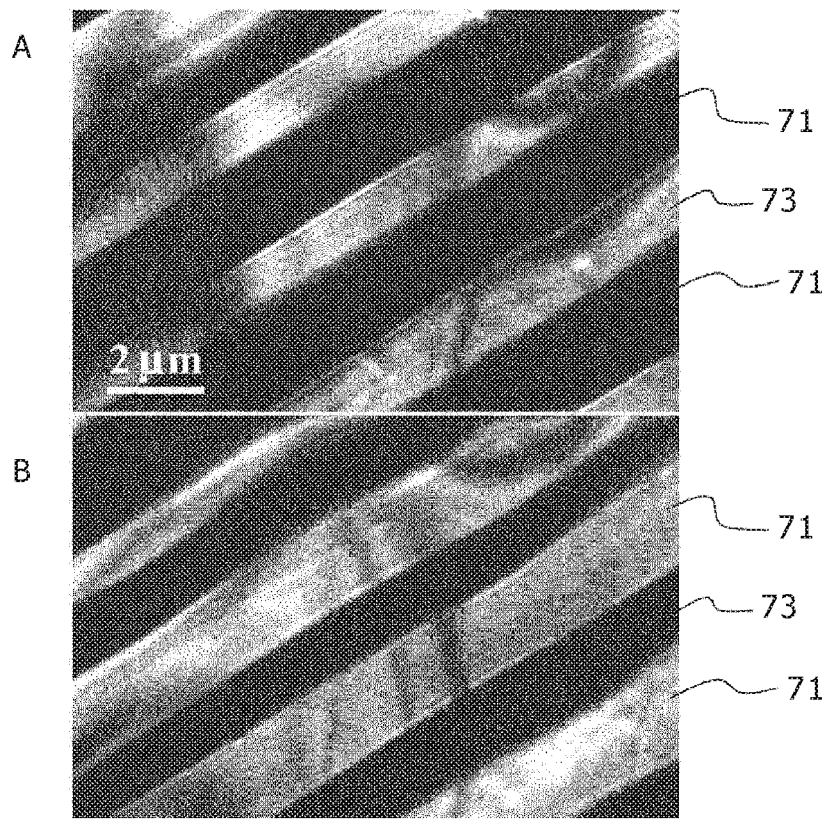
FIG. 20 shows an experimental example of a Foucault image of a 180-degree magnetic domain structure by a lens-less Foucault method.
Figure 21:
FIG. 21 shows an experimental example of a small angle diffraction pattern of a 180-degree magnetic domain structure by a lens-less Foucault method.

FIG. 20 shows an observation example of the Foucault image (in focus) at a location the same as that of FIG. 19, and FIG. 21 shows a small angle electron diffraction pattern which is used for configuring the Foucault image of FIG. 20. A camera length when the small angle diffraction pattern is recorded in FIG. 21 is about 150 m, and becomes an enlarged image of about 200 time magnification in comparison with that when an ordinary Bragg diffraction pattern is observed. Therefore, caution is required that also an angle scale in a diffraction pattern becomes $10^{-5}$ rad.

In the small angle diffraction pattern of FIG. 21, the diffraction spot is separated in two while streaking. It is learned that the 180-degree inversion magnetic domain boundary becomes Bloch magnetic wall since the streak is in a linear shape. FIG. 20A shows a Foucault image observed from a diffraction spot on an upper left side of FIG. 21, and FIG. 20B shows a Foucault image observed from a diffraction spot on a lower right side. Contrasts (71, 73) are inverted respectively with twin boundaries as boundaries, and it is learned that the 180-degree inversion magnetic domain structure in which the magnetic domains are alternately arranged is configured.

In this way, according to the lens-less Foucault method, the small angle diffraction pattern of the same visual field can also be observed along with the Foucault image, and therefore, more experimental knowledge can be obtained than the Fresnel image.

In this way, according to the present invention, even a general use type high resolution electron microscope can directly visualize the magnetic domains by the Foucault method (refer to FIG. 20). Also, when the magnetic wall is observed by the Foucault image, the small angle diffraction pattern can easily be observed, and the small angle diffraction spot can be selected and extracted (refer to FIG. 21).

Figure 22:
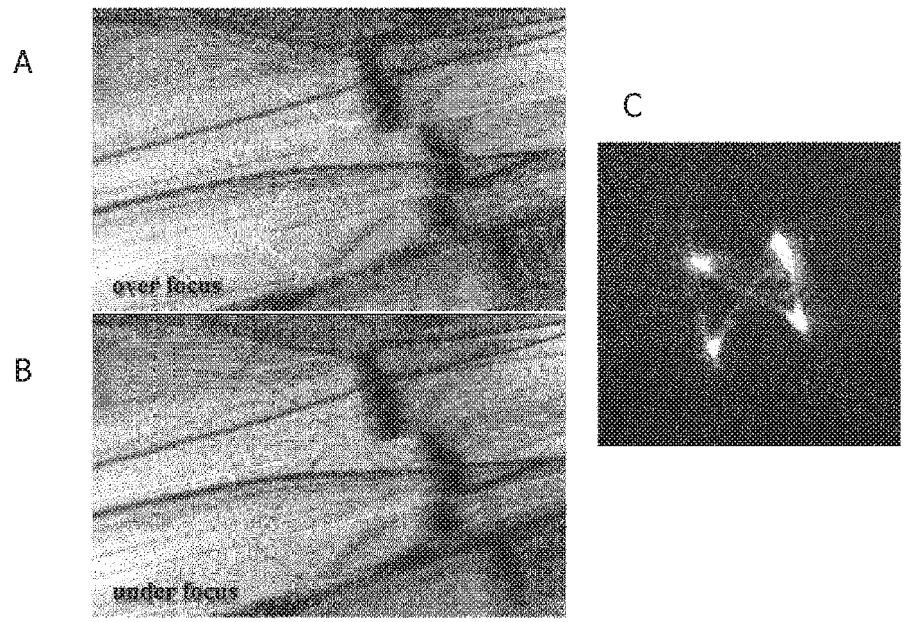
FIG. 22 shows an experimental example of Fresnel images of a 90/180-degree magnetic domain structure by a lens-less Foucault method.

FIG. 22 shows a Fresnel image of the 90-degree/180-degree magnetic domain structure and the small angle electron diffraction pattern. Zigzag magnetic walls in a vertical direction are observed at center portions of FIGS. 22A (under focus) and B (over focus), this is the 180-degree magnetic wall, and linear contrasts extended in a left and right direction from respective apexes of the magnetic walls in the zigzag shape are the 90-degree magnetic walls. FIG. 22C shows small angle diffraction patterns of observation areas of FIGS. 22A and B. Streaks intersected in an X-like shape at a center portion of the diffraction pattern are by the 180-degree magnetic wall, and a streak connecting left and right diffraction spots in an up and down direction is by the 90-degree magnetic wall.

Figure 23:
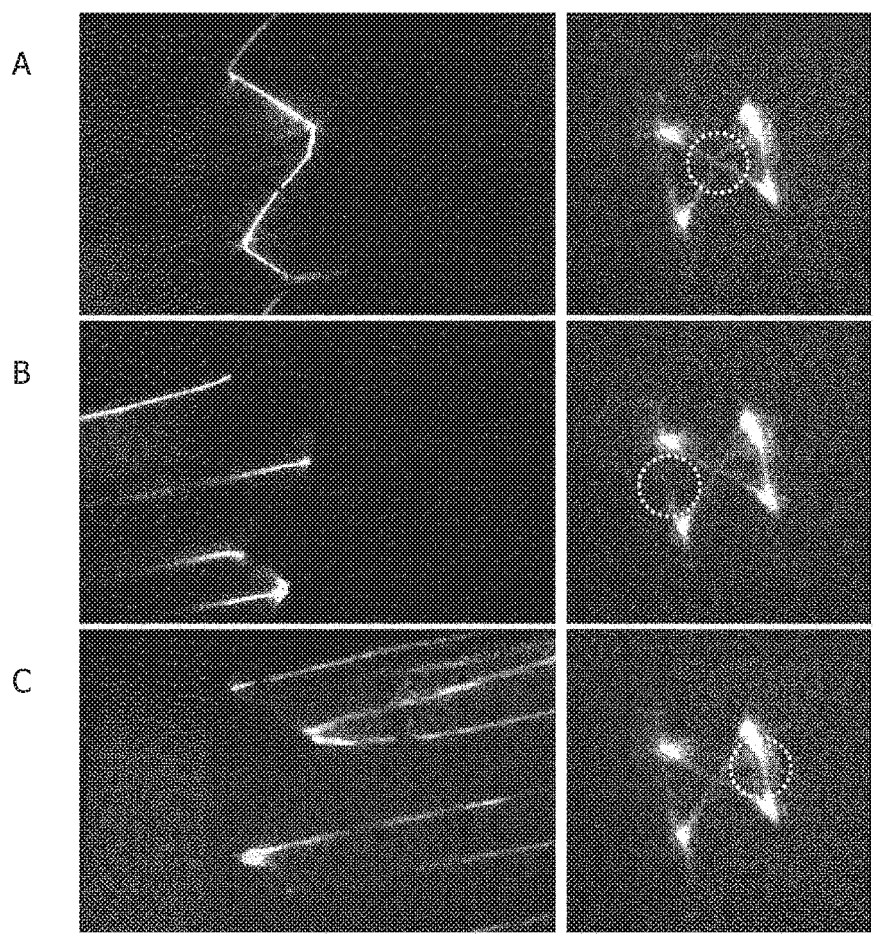
FIG. 23 shows an experimental example of a small angle diffraction pattern in correspondence with a domain wall of a 90-/180-degree magnetic domain structure by a lens-less Foucault method. A: 180-degree magnetic wall. B: 90-degree magnetic wall. C: 90-degree magnetic wall other than B.

FIG. 23 shows a Foucault image of the 90-degree magnetic wall and a streak in a small diffraction pattern selected when the Foucault image is obtained. FIG. 23A shows the Foucault image of the 180-degree magnetic wall of the X-like streak at the diffraction pattern center portion, FIG. 23B shows the Foucault image of the 90-degree magnetic wall of the left side streak of the diffraction pattern, and FIG. 23C shows the Foucault image of the 90-degree magnetic wall on the right side streak of the diffraction pattern. In the Foucault image of FIG. 23, only the magnetic wall is visualized in a linear shape. The visualized magnetic wall differs in accordance with a selected streak, and a particular magnetic wall can be aimed and observed. In this way, even in the Foucault method which has been considered to only observe the magnetic domain ordinarily can observe the magnetic wall directly in focus according to the present method. Further, when the element analysis can be executed by the energy analyzer while confirming the Foucault image of the magnetic wall, an element segregated to the magnetic wall can be found.

LIST OF REFERENCE SIGNS

1: electron source or electron gun, 10: image of electron source (crossover), 11: image of electron source or electron diffraction spot deflected in upper left direction on paper face by sample, 13: image of electron source or electron diffraction spot deflected in upper right direction on paper face by sample, 18: vacuum vessel, 19: control unit of electron source, 2: optical axis, 24: projecting face, 25: intensity distribution of electron beam on projecting face, 27: electron beam or orbit of electron beam, 3: sample, 31, 33: magnetic domains, 32: magnetic wall, 35: focus position on lower side of sample, 36: focus position on upper side of sample, 39: control unit of sample, 4: irradiating optical system (lens system), 40: accelerating tube, 41: first irradiating lens, 42: second irradiating lens, 44: irradiating aperture for STEM, 45: aperture of irradiating optical system, 47: control unit of second irradiating lens, 48: control unit of first irradiating lens, 49: control unit of accelerating tube, 5: objective lens, 51: control system computer, 52: monitor of control system computer, 527: image observation mode means, 528: low amplification image observation mode means, 529: diffraction pattern observation mode means, 53: control panel of control system, 531X: sample inching knob in X direction, 531Y: sample inching knob in Y direction, 532: amplification adjusting knob, 533: irradiating region adjusting knob, 534: irradiation system deflection adjusting knob, 535: focus adjusting knob, 536: Foucault image observation mode means, 537: small angle diffraction pattern observation mode means, 538: adjustment stop releasing means of irradiation optical system, 539: adjustment stopping means of irradiating optical system, 55: objective aperture, 59: control unit of objective lens, 61: first imaging lens, 62: second imaging lens, 63: third imaging lens, 64: projecting lens, 65: selected area aperture, 66: control unit of projecting lens, 67: control unit of third imaging lens, 68: control unit of second imaging lens, 69: control unit of first imaging lens, 71, 73: images of magnetic domains, 72: image of magnetic wall, 75: arithmetic processing device, 76: image display device, 77: image recording device, 78: control unit of observation recording medium, 79: observation recording medium, 8: image face of sample by objective lens, 81: deflector, 82: diffraction pattern, 84: Foucault image, 85: image by electron beam which is not deflected by sample, 86: Fresnel image, 87: control unit of selected area aperture, 88: control unit of deflector, 89: observing and recording face, 90: electron beam biprism, 91: filament electrode of electron beam biprism, 95: EELS, 96: image of energy loss electron which is not deflected by sample, 97: electron optics system of EELS, 98: energy spectrum, 99: image of energy loss electron receiving deflection by sample

The invention claimed is:

1. An electron microscope having a light source of an electron beam,
an irradiating optical system configured by a plurality of electron lenses for irradiating a sample with the electron beam emitted from the light source, a movable irradiation aperture belonging to the irradiating optical system for changing an irradiating amount of the electron beam to the sample,
a sample holding device for holding the sample which the electron beam irradiates,
an imaging lens system configured by the plurality of electron lenses for focusing an image of the sample or a diffraction pattern of the sample,
an observing face for observing the image of the sample or the diffraction pattern of the sample by the imaging lens system, and
a recording device for recording the image of the sample or the diffraction pattern of the sample,
the electron microscope comprising:
a movable first aperture for selectively transmitting a portion of the electron beam transmitting the sample between a first imaging lens disposed at an uppermost stream side in a progressing direction of the electron beam in the electron lens belonging to the imaging lens system and the sample holding device; and
a deflecting device for deflecting the electron beam to a downstream side in the progressing direction of the electron beam of the first imaging lens,
wherein the electron beam transmitting the sample is converged to the first aperture by the irradiating optical system,
an axis deviation of the electron beam generated in accordance with a change in a focal length of the first imaging lens is corrected by the deflecting device, and
the image of the sample and the diffraction pattern of the sample are observed by changing the focal length of the first imaging lens.

2. The electron microscope according to claim 1, wherein a state of the electron lens in charge of changing an irradiating area of the electron beam to the sample in the electron lens belonging to the irradiating optical system is fixed by an operation by an operator of the electron microscope, and the state of the electron lens is continued without depending on another operation of the electron microscope until the state of the electron lens is released by the operation or an operation other than the operation.

3. An electron microscope having a light source of an electron beam, an irradiating optical system configured by a plurality of electron lenses for irradiating a sample with the electron beam emitted from the light source, a movable irradiation aperture belonging to the irradiating optical system for changing an irradiating amount of the electron beam to the sample, a sample holding device for holding the sample which the electron beam irradiates, a imaging lens system configured by the plurality of the electron lenses for focusing an image of the sample or a diffraction pattern of the sample, an observing face for observing the image of the sample or the diffraction pattern of the sample by the imaging lens system, and a recording device for recording the image of the sample or the diffraction pattern of the sample, the electron microscope comprising:
a movable first aperture for selectively transmitting a portion of the electron beam transmitting the sample between a first imaging lens disposed at an uppermost stream side in a progressing direction of the electron beam in the electron lens belonging to the imaging lens system and the sample holding device; and
a deflecting device for deflecting the electron beam to a downstream side in the progressing direction of the electron beam of the first imaging lens,
wherein the electron beam transmitting the sample is converged to the first aperture by the irradiating optical system,
an axis deviation of the electron beam generated in accordance with a change in a focal length of the first imaging lens is corrected by the deflecting device, and
the image of the sample and the diffraction pattern of the sample are observed by changing the focal length of the first imaging lens,
wherein the focal distance of the first imaging lens for observing the image of the sample, and the focal distance of the first imaging lens for observing the diffraction pattern of the sample are switched by the operation other than the operation according to claim 2 by the operator of the electron microscope.

4. The electron microscope according to claim 3, wherein a state of the imaging lens system including the deflecting device required for observing the sample image, and a state of the imaging lens system including the deflection device required for observing the sample diffraction pattern are respectively recorded, and final states of the observations at a previous time in the respective observations are recovered by the switching operation.

5. The electron microscope according to claim 3, wherein the irradiation aperture is not moved.

6. The electron microscope according to claim 1, wherein when any state of the electron lens other than the first imaging lens in the electron lens belonging to the imaging lens system is changed, the focal distance of the first imaging lens is not changed.

7. The electron microscope according to claim 1, wherein the focal length of the first imaging lens can be changed by operating a knob or the like disposed on an operation panel of the electron microscope and included with an intension of adjusting focusing of the image of the sample or the diffraction pattern of the sample by a method clearly described as FOCUS in a state of observing the diffraction pattern of the sample.

8. The electron microscope according to claim 1, wherein the deflecting device can deflect the electron beam in two orthogonal directions on a plane vertical to an optical axis of the electron microscope.

9. The electron microscope according to claim 1, wherein a change of the focal length of the first imaging lens and correction of an axial deviation of the electron beam by the deflecting device are configured to be interlocked by each other.

10. The electron microscope according to claim 1, wherein an electron beam configuring a portion or all of the image of the sample or the diffraction pattern of the sample is introduced into an energy analyzer, and an energy spectrum is measured.

11. The electron microscope according to claim 1, wherein an electron beam configuring a portion of all of the image of the sample or the diffraction pattern of the sample is introduced into the energy analyzer, and the sample image or the diffraction pattern subjected to energy spectroscopy is obtained.

12. The electron microscope according to claim 1, wherein a movable third aperture for restricting the electron beam incident on the imaging lens system is installed between the sample holding device and the first aperture.

13. The electron microscope according to claim 1, wherein a movable second aperture for restricting an area of the electron beam for irradiating the sample is installed between the sample holding device and the irradiating optical system.

14. The electron microscope according to claim 1, wherein an electron beam biprism is arranged at a position of installing the first aperture vertically to an optical axis.

15. An observing method of a sample image or a diffraction pattern executed by an electron microscope including a light source of an electron beam,
an irradiating optical system configured by a plurality of electron lenses for irradiating a sample with an electron beam emitted from the light source,
a movable irradiation aperture belonging to the irradiating optical system for changing an irradiating amount of the electron beam to the sample,
a sample holding device for holding the sample irradiated by the electron beam,
an imaging lens system configured by a plurality of electron lenses for focusing an image of the sample or a diffraction pattern of the sample,
an observing face for observing the image of the sample or the diffraction pattern of the sample by the imaging lens system,
a recording device for recording the image of the sample or the diffraction pattern of the sample,
a movable first aperture for selectively transmitting a portion of the electron beam transmitting the sample between a first imaging lens disposed on an uppermost stream side in a progressing direction of the electron beam in the electron lens belonging to the imaging lens system and the sample holding device, and
a deflecting device for deflecting the electron beam on a downstream side in the progressing direction of the electron beam of the first imaging lens,
wherein the electron beam transmitting the sample is converged to the first aperture by the irradiation optical system,
an axial deviation of the electron beam generated in accordance with a change of the focal length of the first imaging lens is corrected by the deflecting device, and
the image of the sample and the diffraction pattern of the sample are observed by changing the focal length of the first imaging lens.

16. An energy spectrum measuring method executed by an electron microscope including a light source of an electron beam,
an irradiating optical system configured by a plurality of electron lenses for irradiating a sample with the electron beam emitted from the light source,
a movable irradiation aperture belonging to the irradiating optical system for changing an irradiating amount of the electron beam to the sample,
a sample holding device for holding the sample irradiated by the electron beam,
an imaging lens system configured by a plurality of electron lenses for focusing an image of the sample or a diffraction pattern of the sample,
an observing face for observing the image of the sample or the diffraction pattern of the sample by the imaging lens system,
a recording device for recording the image of the sample or the diffraction pattern of the sample,
an operable first aperture for selectively transmitting a portion of the electron beam transmitting the sample between a first imaging lens disposed on an uppermost stream side in a progressing direction of the electron beam in the electron lens belonging to the imaging lens system, and
a deflecting device for deflecting the electron beam on a downstream side in the progressing direction of the electron beam of the first imaging lens,
wherein the electron beam transmitting the sample is converged to the operable first aperture by the irradiating optical system,
an axial deviation of the electron beam generated in accordance with a change of the focal length of the first imaging lens is corrected by the deflecting device,
the image of the sample and the diffraction pattern of the sample are observed by changing the focal length of the first imaging lens, and
the energy spectrum measuring method is executed by introducing the electron beam configuring a portion of all of the image of the sample or the diffraction pattern of the sample to an energy analyzer.

* * * * *